(12) United States Patent
Jones et al.

(10) Patent No.: US 6,823,298 B1
(45) Date of Patent: Nov. 23, 2004

(54) PYROLYTIC OIL-PRODUCTIVITY INDEX METHOD FOR PREDICTING RESERVOIR ROCK AND OIL CHARACTERISTICS

(75) Inventors: Peter J. Jones, Dhahran (SA); Emad N. Al-Shafei, Saihat (SA); Henry I Halpern, Dhahran (SA); Jaffar M. Al-Dubaisi, Dhahran (SA); Robert E. Ballay, Dhahran (SA); James J. Funk, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 09/576,949

(22) Filed: May 23, 2000

(51) Int. Cl.$^7$ ................................................ G06G 7/48

(52) U.S. Cl. ............................................... 703/10

(58) Field of Search ..................... 703/10; 73/152.11; 507/100; 402/6

(56) References Cited

U.S. PATENT DOCUMENTS 5,442,950 A    8/1995  Unalmiser et al. ............. 73/38

Primary Examiner—Kevin J. Teska
Assistant Examiner—Dwin M. Craig
(74) Attorney, Agent, or Firm—Abelman, Frayne & Schwab

(57) ABSTRACT

In the pyrolytic oil-production index method, or POPI method, the numerical values obtained by the application of the prior art POPI method are standardized or normalized. In another aspect, the POPI method and associated data are employed in combination with other empirically determined information to provide values of (1) the API gravity for the reservoir oil; (2) the Apparent Water Saturation ($AS_w$) of the reservoir rock; and (3) the cementation and saturation exponents that are used in the Archie equation for calculating the water saturation in the oil-reservoir rock. This method results in the standardization of the numerical values derived by the POPI method. Applying the normalization or standardization process to the POPI method results in the conversion of the numerical value of $POPI_o$ for good oil-producing reservoir rock to a standard value.

32 Claims, 17 Drawing Sheets

PYROLYTIC OIL-PRODUCTIVITY INDEX METHOD FOR PREDICTING RESERVOIR ROCK AND OIL CHARACTERISTICS

FIELD OF THE INVENTION

This invention relates to the use of data derived from the pyrolytic oil-productivity index, or POPI, to further predict other characteristics of the oil-bearing reservoir rock and the characteristics of the oil in the reservoir.

BACKGROUND OF THE INVENTION

A method for characterizing reservoir rock from the pyrolytic analysis of rock samples known as the Pyrolytic Oil-Productivity Index Method, or "POPI method", is disclosed in U.S. Pat. No. 5,866,814. The disclosure of U.S. Pat. No. 5,866,814 is incorporated herein in its entirety by reference.

In the practice of the POPI method, the quality of the reservoir rock at a given location and depth is characterized as (a) oil-producing; (b) marginally oil-producing; or (c) non-reservoir or tar occluded. These relative characterizations are based on a comparison of the value of $POPI_X$ for a given rock sample X with the value of $POPI_o$ that has been previously determined from either (1) oil-stained reservoir rock samples similar to the drilling target that are known to be of good reservoir quality; or (2) a sample of oil that is similar to the expected composition of the well's target zone. The principal advantage of the POPI method is its ability to provide data in real time based on cutting samples taken from the drill rig, so that on-the-fly changes can be made, e.g., in horizontal drilling directions, to keep the bit in oil-producing reservoir rock. The POPI method can also be used to amass a body of comparative data for a given region or an oil field that can be used in planning further exploration and production.

The analytical procedures for determining the values for POPI are described in U.S. Pat. No. 5,866,814 (Jones and Tobey), and in view of the relationship of the present invention to the POPI method, the following summary is provided to facilitate an understanding of the terminology and significance of the data points.

1. Definitions

As used in this specification and claims, the following terms have the meanings indicated:

HC means hydrocarbons.

ln means natural logarithm.

LV is the weight in milligrams of HC released per gram of rock at the static temperature condition of 180° C. (when the crucible is inserted into the pyrolytic chamber) prior to the temperature-programmed pyrolysis of the sample.

TD is the weight in milligrams of HC released per gram of rock at a temperature between 180° C. and $T_{min}$° C.

TC is the weight in mg of HC released per gram of rock at a temperature between $T_{min}$° C. and 600° C.

LV+TD+TC represents total HC vaporizing between 180°–600° C. A low total HC indicates rock of lower porosity or effective porosity. A low value can also indicate zones of water and/or gas.

$POPI_o$ is the value of the pyrolytic oil productivity index as calculated for a representative sample of crude oil of the type which is expected to be found in good quality reservoir rock in the region of the drilling and chosen as a standard.

$T_{min}$(° C.) is the temperature at which HC volatization is at a minimum between the temperature of maximum HC volatization for TD and TC and is empirically determined for each sample. Alternatively, a temperature of 400° C. can be used for samples where there is no discernable minimum between TD and TC. The latter sample types generally have very low total HC yields.

Phi is the average porosity of the rock.

Sxo is the saturation of drilling mud filtrate and represents the amount of HC displaced by the filtrate, and therefore, movable HC.

Phi*Sxo vs depth plot—the area below the curve represents the proportion of porosity which contains movable HC.

Phi vs depth plot—the area between the Phi curve and the Phi*Sxo curve represents immovable HC, or tar.

Gamma—the naturally occurring gamma rays that are given off by various lithologies while measuring directly in the well bore by the prior art petrophysical tools and are reported in standard API (American Petroleum Institute) units.

Caliper—the measured diameter of the well bore taken at the time of running petrophysical logs.

Density porosity—the porosity calculated by prior art methods from the petrophysical bulk density tools using an assumed fluid and grain density.

Neutron porosity—the porosity measured by prior art methods from petrophysical neutron tools.

Deep resistivity—the resistivity measured by deep invasion (long spacing between source and receiver), lateral log or induction petrophysical tools which is used as a measurement of undisturbed formation resistivity.

Medium resistivity—the resistivity measured by medium invasion (medium spacing between source and receiver), lateral log or induction petrophysical tools which is used as a measurement of resistivity of the formation that has been flushed by mud filtrate from the drilling fluid.

Shallow resistivity—the resistivity measured by shallow invasion (short spacing between source and receiver), lateral log or induction petrophysical analytic techniques which is used as a measurement of the resistivity of the mud filtrate from the mud cake that forms on the interior of the well bore during drilling operations.

Neutron-density cross-plot porosity (N-D Phi)—the porosity determined from a common prior art method which compensates for the effects of lithologic and fluid changes that lead to inaccuracies in employing either density or neutron porosity measurements by themselves.

Core plug permeability—the permeability measured by prior art methods from cylindrical rock samples that are cut from cores taken from the drilling process that is reported in units of millidarcys (md).

2. Pyrolysis Analytical Procedure

The analytical method used to quantitatively determine the presence of hydrocarbons in reservoir rock samples is known as open-system pyrolysis. In the practice of the POPI method of the invention the following expression is used to provide one or more data points:

$$\ln(LV+TD+TC) \times (TD \div TC) = POPI \qquad (I)$$

In the above expression, the term "ln(LV+TD+TC)" means the natural logarithm of the value and the term "POPI" is used as shorthand for Pyrolytic Oil Productivity Index. The term POPI is also used more broadly hereinafter as a reference to the method of the invention.

In the POPI method for pyrolysis, a time and temperature-programmed instrument heats a small amount of ground rock sample from a starting temperature of 180° C. (held for 3 minutes) to 600° C. at a rate of increase in temperature of 25° C. per minute. During the programmed heating, the hydrocarbons driven from the rock are recorded as a function of temperature. FIG. 1 shows a typical instrument output plot, which is known as a "pyrogram". A typical analysis results in three peaks. The first is composed of hydrocarbons that can be volatized, desorbed, and detected at or below 180° C. while the temperature is held constant for the first 3 minutes of the procedure. These are called light volatile hydrocarbons, or "light volatiles" (LVHC, or LV). The next phase of the pyrolytic analysis consists of a programmed temperature increase from 180° C. to 600° C. that usually results in two more distinct peaks. The first of these peaks occurs between 180° C. and about 400° C., and corresponds to thermal desorption of solvent-extractable bitumen, or the light oil fraction. These are called thermally distilled hydrocarbons (TDHC, or TD). The second peak in this phase (third peak overall) occurs after about 400° C., generally after a minimum in pyrolytic yield is observed and extends typically to about 550° C. The temperature corresponding to the minimum in pyrolytic yield between TD and TC is referred to as $T_{MIN}$. This peak is due to the pyrolysis (cracking) of heavier hydrocarbons, or asphaltenes. The materials that thermally crack are called thermally cracked hydrocarbons or "pyrolyzables" (TCHC, or TC).

As will be understood by those familiar with the art, many other types of data are employed in the characterization of reservoir rock and the oil in the reservoir for the purposes of modeling exploration and production. It is therefore an object of the invention to provide improved methods for determining the characteristics of reservoir rock and the oil in the reservoir based on the POPI method.

It is another object of the invention to provide an improved method for determining reservoir rock characteristics relating to water saturation and to API oil gravity that is less expensive, faster and of comparable accuracy to methods known in the prior art.

It is yet another object of the invention to provide an improved method for determining apparent water saturation values ($AS_w$) from preserved core samples and from core samples that have not been specially preserved, and also by a method that is not dependent on data obtained from petrophysical or electric log data.

Another object of the invention is to provide an improved method that will serve as a substitute for the Dean-Stark method and apparatus for estimating water saturation.

Yet another object of the invention is to provide an improved method of determining water saturation that is both qualitative and quantitative and which is superior to the Dean-Stark calculations when the reservoir contains inhomogeneities, light oil, and/or oil-water transition zones.

A further object of the invention is to provide an improved laboratory method that closely matches the water saturation $S_w$ value as determined by calculation from electric log data employing the Archie equation.

A further object of the invention is to provide a method for assessing changes in the saturation and cementation exponents that are required in utilizing the Archie equation.

SUMMARY OF THE INVENTION

The above objects and other advantages are achieved by the improvements of the invention in the pyrolytic oil-production index method, or POPI method. In accordance with one aspect of the invention, the numerical values obtained by the application of the prior art POPI method are standardized or normalized.

In another aspect of the invention, the POPI method and associated data are employed in combination with other empirically determined information to provide values of (1) the API gravity for the reservoir oil; (2) the Apparent Water Saturation ($AS_w$) of the reservoir rock; and (3) the cementation and saturation exponents that are used in the Archie equation for calculating the water saturation in the oil-reservoir rock.

The improved method of the invention results in the standardization of the numerical values derived by the POPI method. Applying the normalization or standardization process to the POPI method results in the conversion of the numerical value of $POPI_o$ for good oil-producing reservoir rock to a standard value, e.g., 100, which is denominated $POPI_{NORM}$; a sample considered to be non-reservoir rock has a numerical value less than 50 (i.e., less than one-half the original value of $POPI_o$); and sample values from 1/2 $POPI_o$ to $POPI_o$ that are considered to be marginally productive reservoir rock have corresponding numerical values, i.e., between 50 and 100. This normalization or standardization of $POPI_o$ values has several advantages over the method of the prior art, including that of providing a basis for making direct comparisons between and among the indices for different wells and/or regions.

The Pyrolytic Oil-Productivity Index (POPI) method of the prior art is improved in accordance with the invention to utilize a normalized scale, referred to as $POPI_{NORM}$, that is based on a standardized value that indicates good to excellent oil-productivity for the reservoir rock. In a preferred embodiment, the standardized or normalized value is 100. As will be apparent to one of ordinary skill in the art, another value, e.g., 1000, can be used for the purpose of the invention. However, a value of 100 provides a convenient normalization value for the use and analysis of the data. The method comprises the steps of calculating a normalization factor, $F_{NORM}$, that is applied to the POPI values that were calculated in accordance with the method of the prior art. The improved method for determining cut-off values for POPI renders POPI data easier to compare from well to well and from field to field.

The invention also comprehends three related improved methods that enhance the range of information available for the characterization of oil reservoirs. The first is the method for predicting the API gravity of an oil in a reservoir by direct calculation from a series of POPI measurements on non-preserved cores or cuttings.

The second method of the invention is directed to the calculation of the in-reservoir water saturation ($S_w$) value from pyrolysis of reservoir rock samples that are derived from either non-preserved cores or fresh rock cuttings recovered at the drill site. The practice of the method is cost-effective, rapid and is not labor intensive, allowing a large number of samples to be processed for an individual well. The end result is an Apparent Water Saturation ($AS_w$) curve produced by direct measurements that can be compared to water saturation ($S_w$) as calculated by the Archie Equation from indirect down-hole electric log data.

The third improved method is an extension of the determination of the Apparent Water Saturation ($AS_w$). Using the $AS_w$ curve, inferred values for the cementation exponent (m) and the saturation exponent (n) are calculated from the electric log data that satisfy the Archie Equation, as well as the pyrolytic data ($AS_w$). The magnitude of the variation of the m and n values compares favorably to the variations present in direct petrophysical measurements on core samples. These values are extremely useful in developing accurate reservoir models, as well as for estimating reservoir reserves. These improved methods have utility as calibration tools for developing additional input data used in reservoir modeling.

BRIEF DESCRIPTION OF THE FIGURES

The invention and its preferred embodiments will be further described with reference to the attached figures in which.

DETAILED DESCRIPTION OF THE INVENTION

Figure 1:
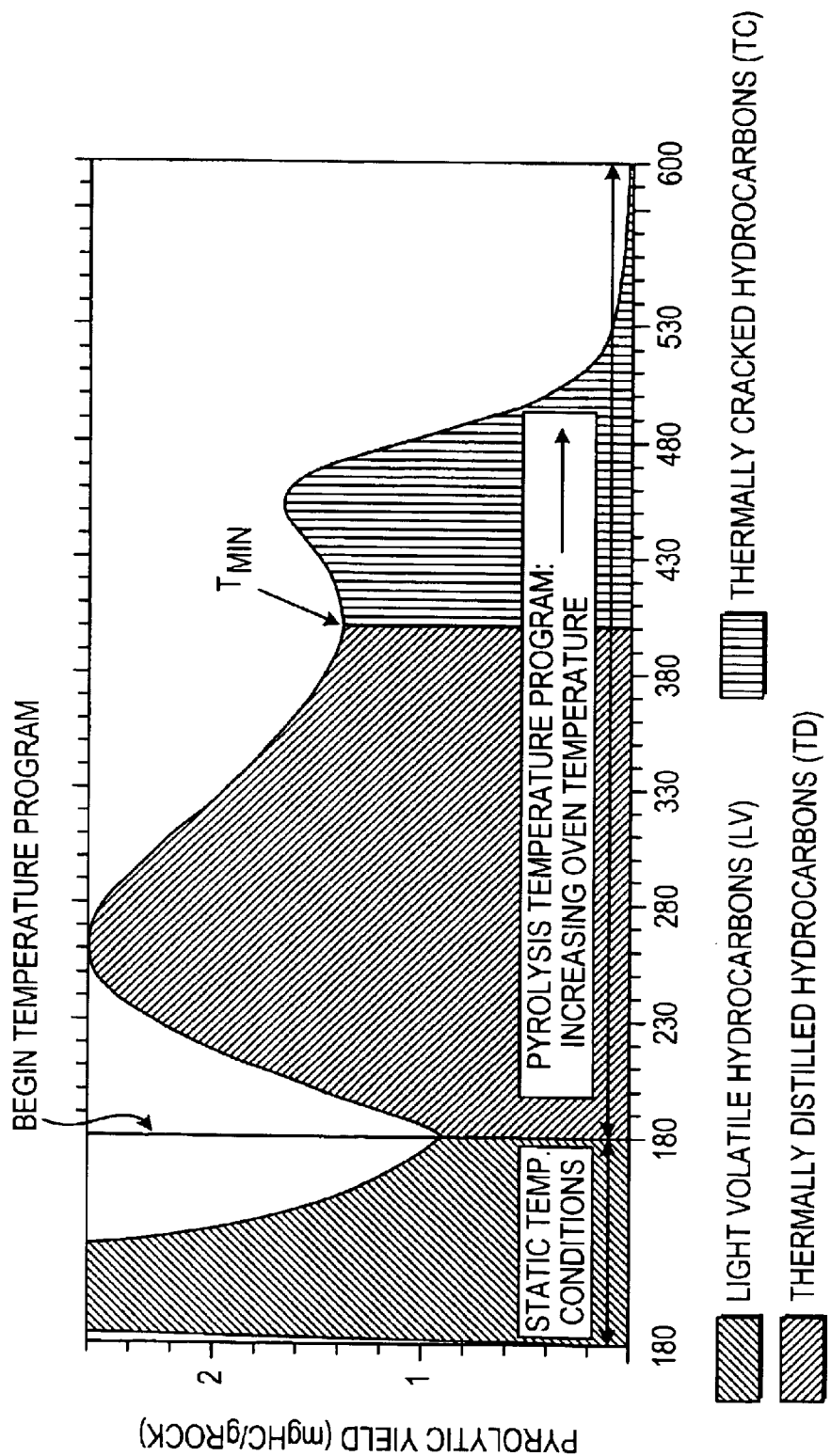
FIG. 1 is a typical prior art program from an open-system temperature-programmed pyrolysis of an oil sample, indicating the areas associated with the data used to calculate the POPI values in accordance with formula (1)

The various aspects and embodiments of the invention are described with reference to the attached drawings sheets in which the figures are comprised of graphs or plots of data or data sets that are based on empirical information for actual wells. The information is believed to be representative for the purposes of describing the improved methods of the invention. As will be understood by one of ordinary skill in the art of developing and interpreting such geophysical data for the purposes of characterizing reservoir rock and its petroleum contents, marked variations do occur between regions, and even within regions due to geological anomalies. In any event, the detailed description of the invention, when read in conjunction with the drawing figures, provides a teaching sufficient to put one of ordinary skill in possession of the invention.

Normalization of POPI Values

In order to provide a standard set of values for the POPI obtained from numerous well sites in a region, or to enable a ready comparison of data from several geophysical and/or geographical regions, a normalization function is applied to the POPI values.

By way of example, and for the purpose of describing the preferred embodiment of the invention, the normalized value for $POPI_o$ is designed to have a value of 100. It will be understood that the value of $POPI_o$ for any given set of pyrolytic data is determined in accordance with the method described in U.S. Pat. No. 5,866,814, and above.

The practice of the improved method of the invention comprises the steps of:

(a) determining the value of $POPI_o$ in accordance with the prior art equation $$POPI_o = \ln(LV+TD+TC) \times (TD \div TC); \quad (1)$$

(b) calculating the value of the normalization factor $F_{NORM}$ in accordance with the following equation (2):

$$F_{NORM} = \frac{100}{POPI_o}; \quad (2)$$

(c) normalizing the value of $POPI_X$ derived from a given rock sample "X" in accordance with the following equation (3A):

$$POPI_{NORM(X)} = F_{NORM} \times POPI_X; \quad (3A)$$

and (d) recording the value of $POPI_{NORM(X)}$.

This normalization process is repeated for values obtained for rock sample "Y" and for the POPI data obtained for all samples in the desired set of samples. Thereafter, the data can be manipulated as desired, and printed in graphic or tabular form. From the above, it will be understood that negative POPI values remain negative; however, they become larger negative numbers, and they still indicate a hydrocarbon saturation that is too low to be within an oil column, thus being either wet, in a gas zone, or in very tight rock. The advantage of this new analysis regimen is to make POPI more amenable to direct comparison between wells with substantially different oil characteristics.

Calculation of API Gravity from POPI Data

As noted above, $POPI_o$ is the Pyrolytic Oil-Productivity Index value that is expected for a rock sample with good reservoir quality given that it is sufficiently high in the oil column to be free from the oil-water transition zone, and that the characteristics of the produced oil are consistent with those that were anticipated. Previously, two principal methods were used to determine the value of $POPI_o$. One method of determining the value of $POPI_o$ was to analyze a series of samples from a reservoir, determine the POPI value for each of the samples, produce a POPI versus depth plot for the set of samples and then compare the POPI values to reservoir quality as determined by conventional electric logs. In doing this, those areas with good reservoir quality usually have a range of POPI values, the minimum of which can be used to separate good quality reservoir rock (i.e., a higher POPI value) from the lower quality reservoir rock (i.e, a lower POPI value).

Figure 2:
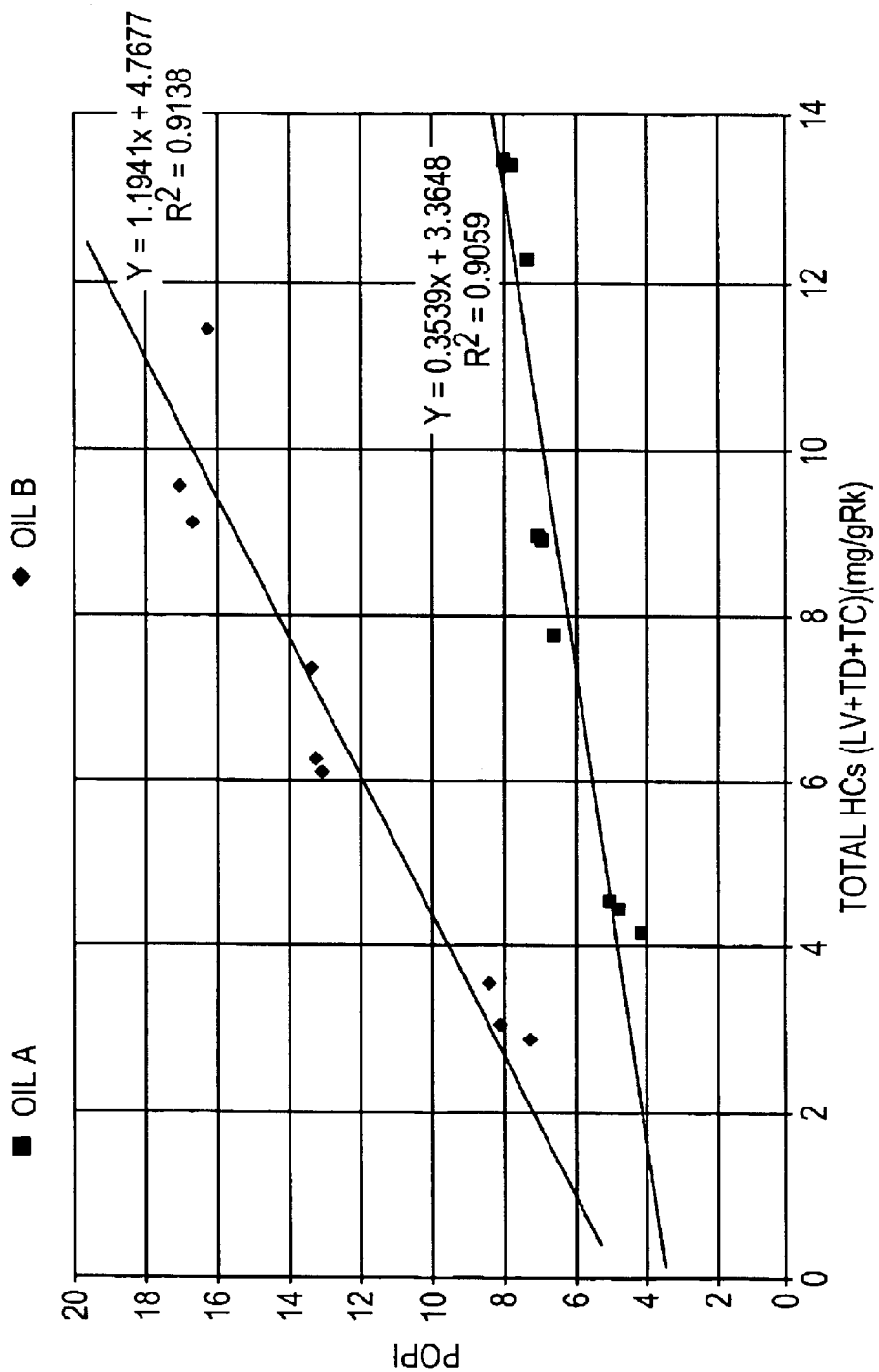
FIG. 2 is a plot of POPI versus Total Hydrocarbons (LV+TD+TC) showing prior art linear interpolations to determine $POPI_o$ for two different oils.

The other method used to determine $POPI_o$ was through an analysis of oil that is similar to the oil actually produced, or that is expected to be produced, in the region from which the rock or core samples to be tested were obtained. The latter procedure is outlined below:

1) To 1 cc of the oil sample, add 9 cc of a suitable solvent, such as methylene chloride, dimethyl sulfide or other suitable solvent that will completely dissolve the oil sample and that is readily evaporated at or below 60° C.
2) Prepare 9 steel crucibles with approximately 100 mg of clean silica gel.
3) Apply to the silica gel, e.g., by a syringe, three samples each of the solution of the oil in solvent quantities of 10, 20 and 30 microliters.
4) Dry the samples at 60° C. in the crucibles in a vacuum oven for 4 hours.
5) Subject the samples to pyrolytic analysis, using 100 milligrams as the required input sample size for the instrument to provide data corresponding to LV, TD, and TC.
6) Utilize standard spreadsheet and graphics software to input the data and prepare a chart or plot (such as that of FIG. 2) with the y-parameter being the POPI value and the x-parameter being the sum of total hydrocarbons (LV+TD+TC).
7) Select the range for the value of $POPI_o$ from the chart where the value of total hydrocarbons is between 4–6 milligrams per gram of sample.

According to the disclosure of U.S. Pat. No. 5,866,814, column 7, lines 30–39, it was understood that a total hydrocarbon value in the range of from 4–6 milligrams was fairly typical for residual staining after sample preparation from oils that are less than 42° API gravity. It was also taught that lighter oils having higher API gravity values could require the use of lower values for total hydrocarbons, since the residual hydrocarbon staining could be significantly lower due to evaporation of the light components and lower amounts of the medium and heavy components. Therefore, it was stated that evaluation of good quality and productive reservoir rock was the preferred means for determining the value of POPI for those reservoirs yielding oil having an API gravity greater than 42°.

Figure 3:
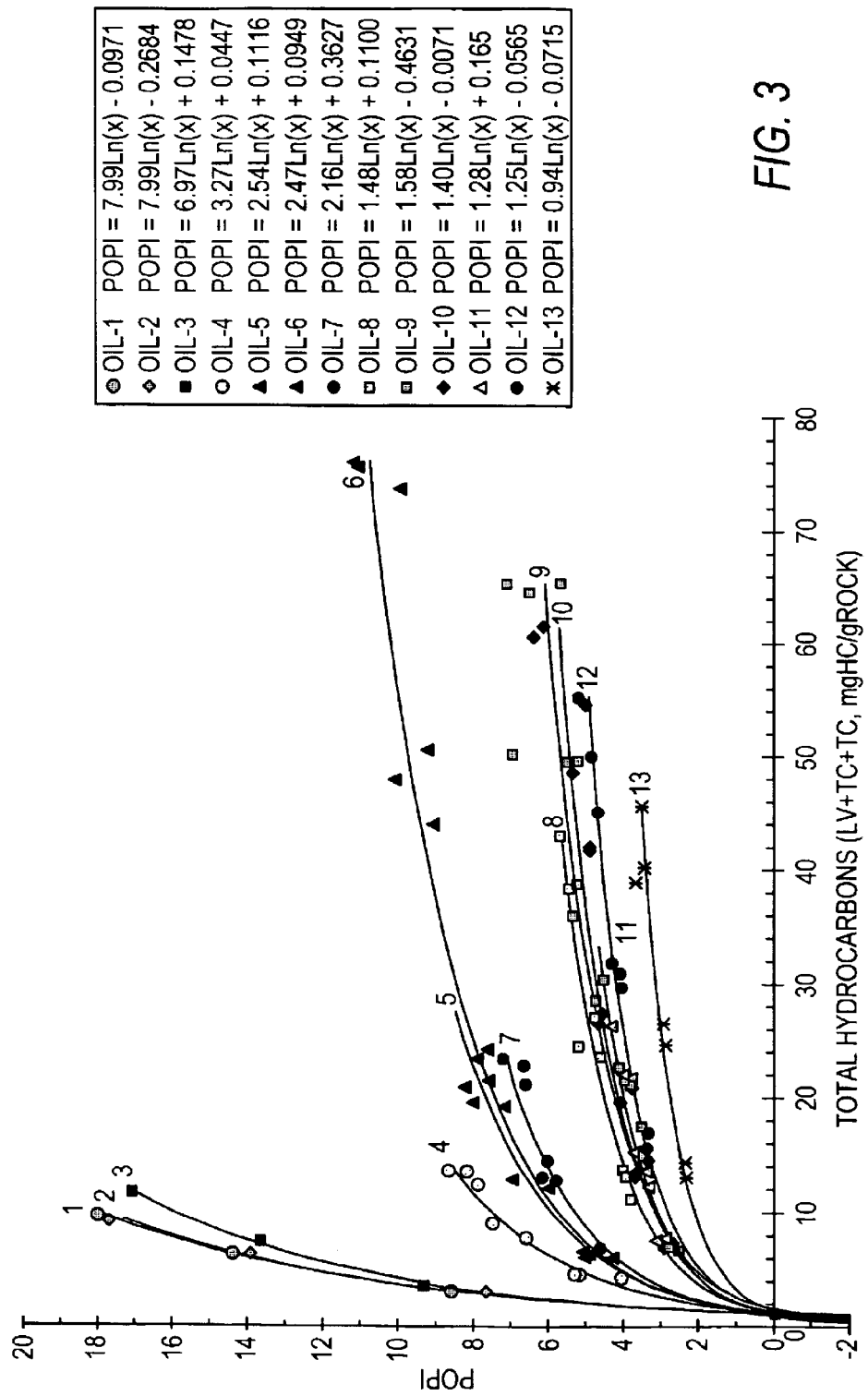
FIG. 3 is a series of plots of POPI versus Total Hydrocarbons (LV+TD+TC) for a suite of oils with substantially different pyrolytic character.

A more accurate understanding of the relation between the change in the POPI value with changes in oil characteristics has now been determined as a result of the analysis of a large number of crude oil and rock samples. FIG. 3 is a plot of POPI values versus total hydrocarbons (LV+TD+TC) for a set of oil samples that were analyzed by the procedure of steps (1) through (7) as set forth above. In this sample set, the samples ranged in volume from 10, 20 and 30 microliters and included some samples of up to 80 micro-liters. As will be seen from FIG. 3, the striking characteristic of the plot of the test data is that the best-fit for the variation of POPI is not linear, as previously suggested by FIG. 2 of the prior art, but rather, the trend of the data is logarithmic. This is apparently attributable to the fact that the POPI calculation includes the natural logarithm of the total hydrocarbons in its equation.

Figure 4:
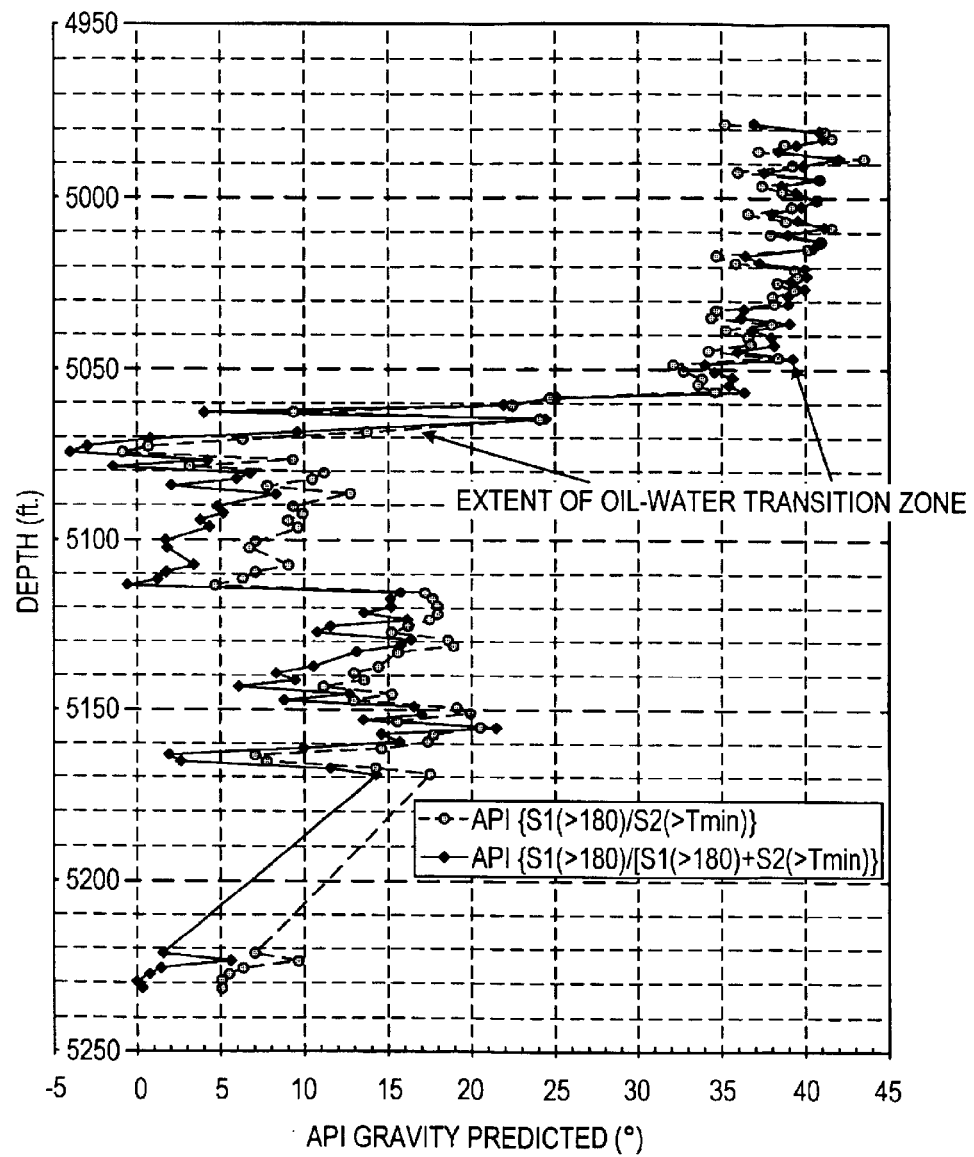
FIG. 4 is a plot of depth versus predicted API gravity based on pyrolytic data ratios for individual core samples.

Various other methods of estimating API gravity values from pyrolytic data have been developed. These methods have a common feature in that they produce a separate API gravity determination for each sample analyzed. Moreover, when considering a well profile, these predicted API gravities show considerable variation, especially when an oil-water transition zone is encountered as shown for the example in FIG. 4. However, during production of a well, a single API gravity is generally representative of the produced oil.

Based on this practical determination, the relationship is established for each of these oil samples by the following equation (4):

$$POPI = PPLC \times \ln(LV+TD+TC) + b \tag{4}$$

where
PPLC is the POPI Pre-Logarithmic Coefficient and is a constant for a given type of oil;
ln is the natural logarithm;
(LV+TD+TC) is the total quantity of hydrocarbons in a sample; and
b is an empirically determined constant.

It has been found empirically that the constant b is typically less than about 0.1, and since variations in POPI of this magnitude are not significant, the value of b can be disregarded. Thus, for the purpose of the practice of the invention, the above equation (2) is simplified to equation (5):

$$POPI_{oil} = PPLC \times \ln(LV+TD+TC) \tag{5}$$

where $POPI_{oil}$ is the value of POPI obtained by varying concentrations of oil on either a silica gel substrate or on reservoir rock samples; and the other terms are as defined above.

Figure 5:
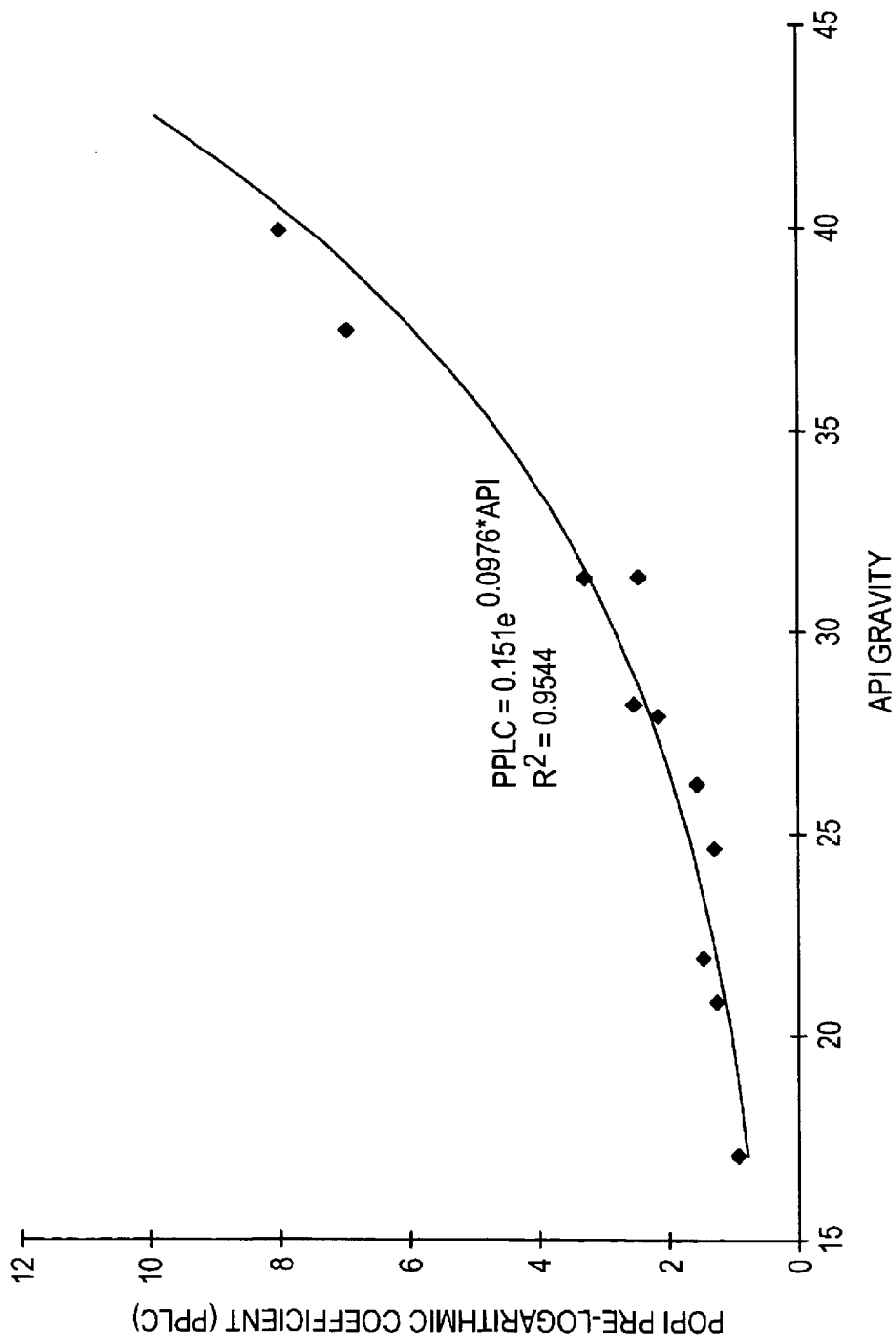
FIG. 5 is a plot of the POPI Pre-Logarithmic Coefficient versus API Gravity for the oils of FIG. 3.

The values of $POPI_{oil}$ at various concentrations are plotted to provide a trend line, the shape or curve of which reflects the characteristics of the oil. From equations (4) and (5) above, it will be understood that it is the PPLC that determines the shape of the curve resulting from the plot of POPI versus total hydrocarbons. In accordance with another aspect of the invention, the value of the PPLC, and hence the shape of the curve, is directly related to the API gravity of the reservoir oil. FIG. 5 is a plot of the PPLC versus the API gravity of the various oil samples. As can be seen, the plot of PPLC versus API gravity data exhibits an excellent exponential fit, with a high correlation coefficient r=0.967. As a result, API gravity alone can be used to calculate the value of the PPLC; conversely, the PPLC can be used to calculate API gravity. The validity of this relationship was established by comparisons of empirical data from a geographically large oil production region. As will be understood by one of ordinary skill in the art, other basins or regions may require the determination of their own specific values. However, the principles and underlying behavior of the equation are the same. Therefore, steps to develop alternative relationships for other basins result in relatively minor overall differences. Thus, for a given data set, the following equation (6) can be used for determining the PPLC:

$$PPLC = PEC \times e^{(c \times API)} \tag{6}$$

where
PEC is the pre-exponential coefficient (determined empirically from the data to be about 0.151);
e is the base value for the natural logarithm (an irrational number with a decimal approximation of 2.718281);
c is a constant (determined empirically from actual field data to be about 0.0976); and
API is the numerical value of the API gravity.

Substituting the numerical values in (6) above:

$$PPLC = 0.151 \times e^{(0.0976 API)} \quad (6A)$$

This equation can be solved for API gravity in terms of PPLC as:

$$API = [\ln(PPLC/PEC)]/c, \quad (6B)$$

or $$API = [\ln(PPLC/0.151)]/0.0976 \quad (6C)$$

From equations 6 and 6A–6C above, a variety of relevant information can be determined. First, $POPI_o$, the cut-off value for POPI that is consistent with good reservoir quality, can be calculated from the API gravity alone using a simplified version of equation (6). Since the constant in equation (4) is negligible, then:

$$POPI_o = PPLC \times \ln(HC_{MIN}) \quad (7)$$

where $HC_{MIN}$ is the minimum quantity of residual hydrocarbon staining for good quality reservoir rock located above an oil-water transition zone.

Figure 6:
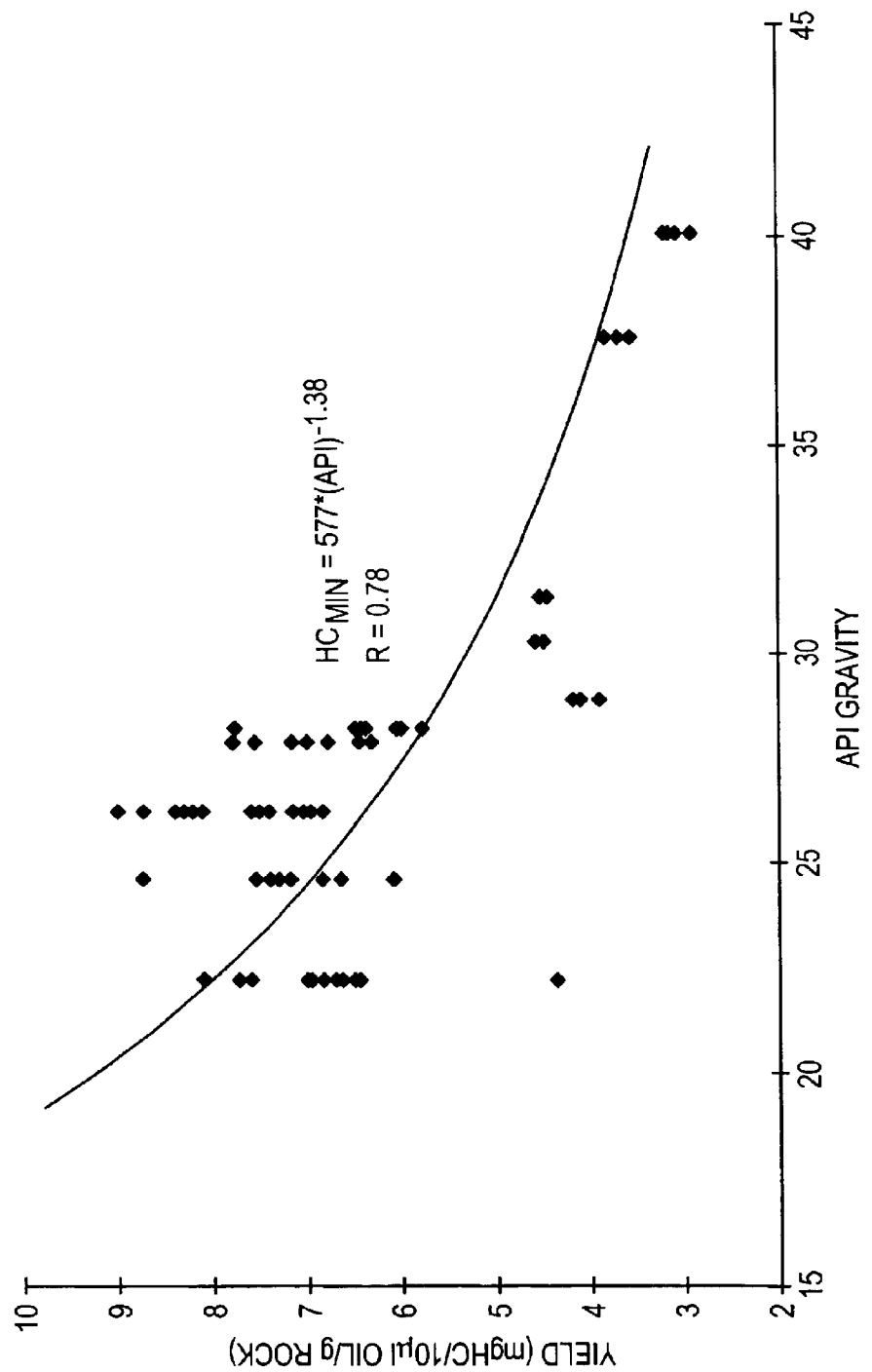
FIG. 6 is a plot of pyrolytic yield versus API gravity.

As previously noted, based on empirical data, this value is between 4–6 milligrams of total pyrolytic yield (LV+TD+TC) gram of rock. Results of oil analyses have also yielded a method for estimating $HC_{MIN}$ from the actual anticipated API gravity of a sample. FIG. 6 is a cross-plot of total pyrolytic yield (LV+TD+TC) per 10 microliters of oil sample versus API gravity. The data show that with increasing API gravity, the expected yield for the same quantity of original hydrocarbons decreases. This is due to evaporation of the lighter components, especially LV, in the higher gravity samples. The POPI value derived from pyrolytic data from a reservoir containing 31° API gravity oil on this plot yields a value of 5 milligrams total HC/microliter of oil. Therefore, in good quality reservoir rock, after accounting for the effects of flushing the rock with mud filtrate and the sample preparation, only staining, representative of 10 microliters per gram of original in-reservoir oil remains. Of the remaining residual hydrocarbons, the total yield varies with the API gravity in accordance with the following:

$$HC_{MIN} = 577 \times API^{-1.38} \quad (8)$$

Using this relationship, $HC_{MIN}$ is substituted in equations (5) or (7) to solve for the POPI cut-off value for good quality reservoir rock as follows:

$$POPI_o = PPLC \times \ln(577 \times API^{-1.38}) \quad (9)$$

Figure 7:
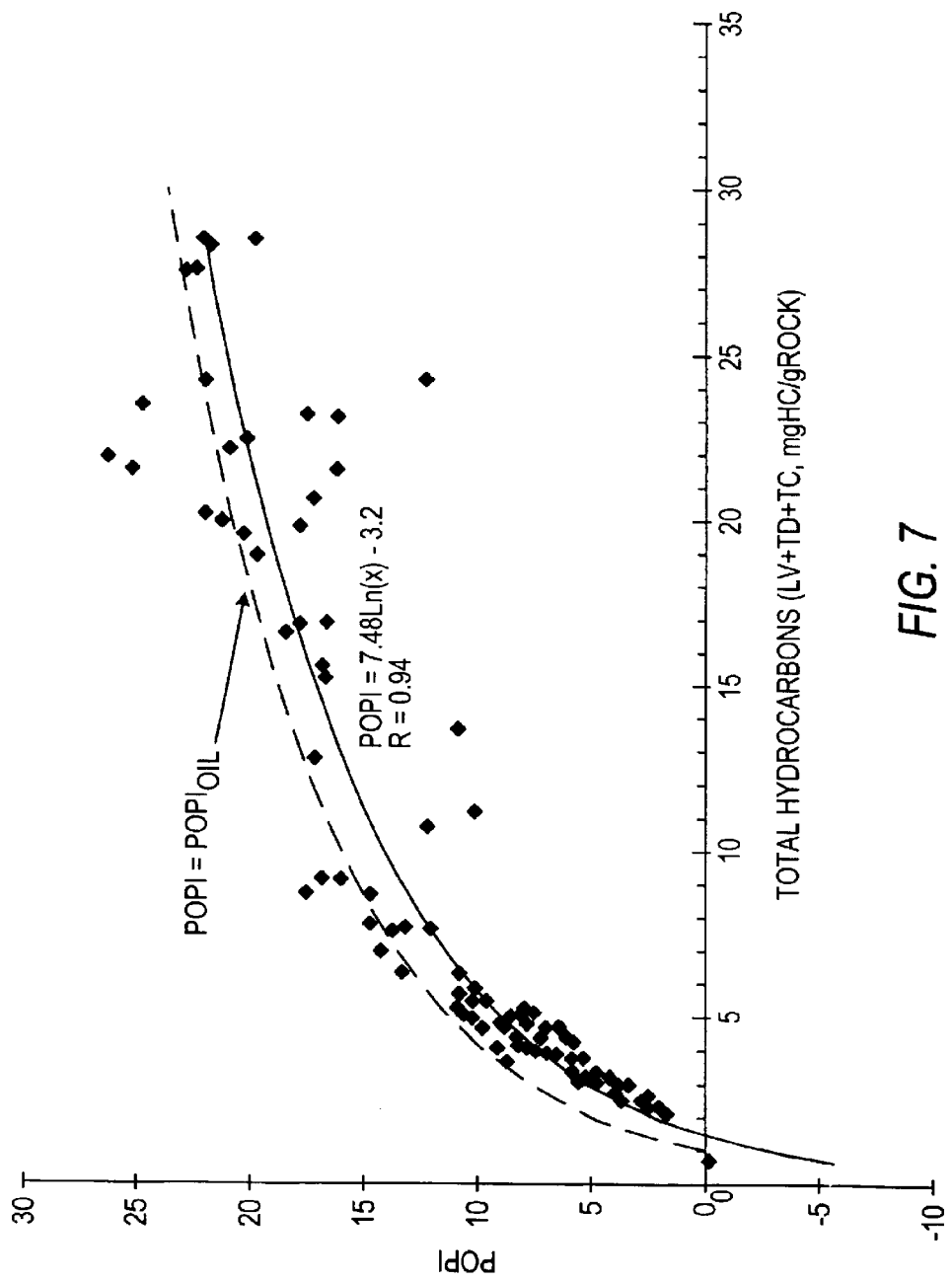
FIG. 7 is a plot of POPI versus Total Hydrocarbons (LV+TD+TC) for a well-behaved data set of reservoir rock samples.

PPLC, and hence $POPI_o$, can then be determined either through data analysis on a set of samples, or by solving equation (6) using API gravity. FIG. 7 is a typical cross plot of POPI values versus total hydrocarbon yield (LV+TD+TC) that exhibits a well-behaved set of data from reservoir rock samples. In this case, the solid curve is the logarithmic trend line generated from the data set and can be expressed by the equation:

$$POPI = 7.48\ln(\text{Total Hydrocarbons}) - 3.2 \text{(correlation coefficient } r=0.94).$$

The dashed curve is a hypothetical line that represents an oil with the same PPLC as the rock data (approximately 7.5), and an insignificant constant b. This curve is representative of the curve that is generated by the actual oil sample, that is $POPI = POPI_{oil}$, where $POPI_{oil}$ is the POPI value that the oil would have given at any total hydrocarbon yield. Thus, the PPLC as determined by plotting these data can now be used in equation (7) to calculate $POPI_o$, and if the API gravity is unknown, then it can also be determined through equation (6) and then used for estimating $HC_{MIN}$ in equation (8).

As shown above, API gravity can also be estimated through the analysis of POPI data. For a set of data generated from either an oil sample (using the above method for determining $POPI_o$ from oil samples, e.g., as in FIG. 3) or from core or drill cutting samples, a plot of POPI versus total hydrocarbons (LV+TC+TC) is generated, as in FIG. 7. From this plot, the POPI Pre-Logarithmic Coefficient (PPLC) is obtained by fitting the data to a logarithmic curve. As shown in FIG. 5, the PPLC has an excellent exponential fit when plotted against API gravity, and expressed by equation (3), (correlation coefficient r=0.98).

Figure 8:
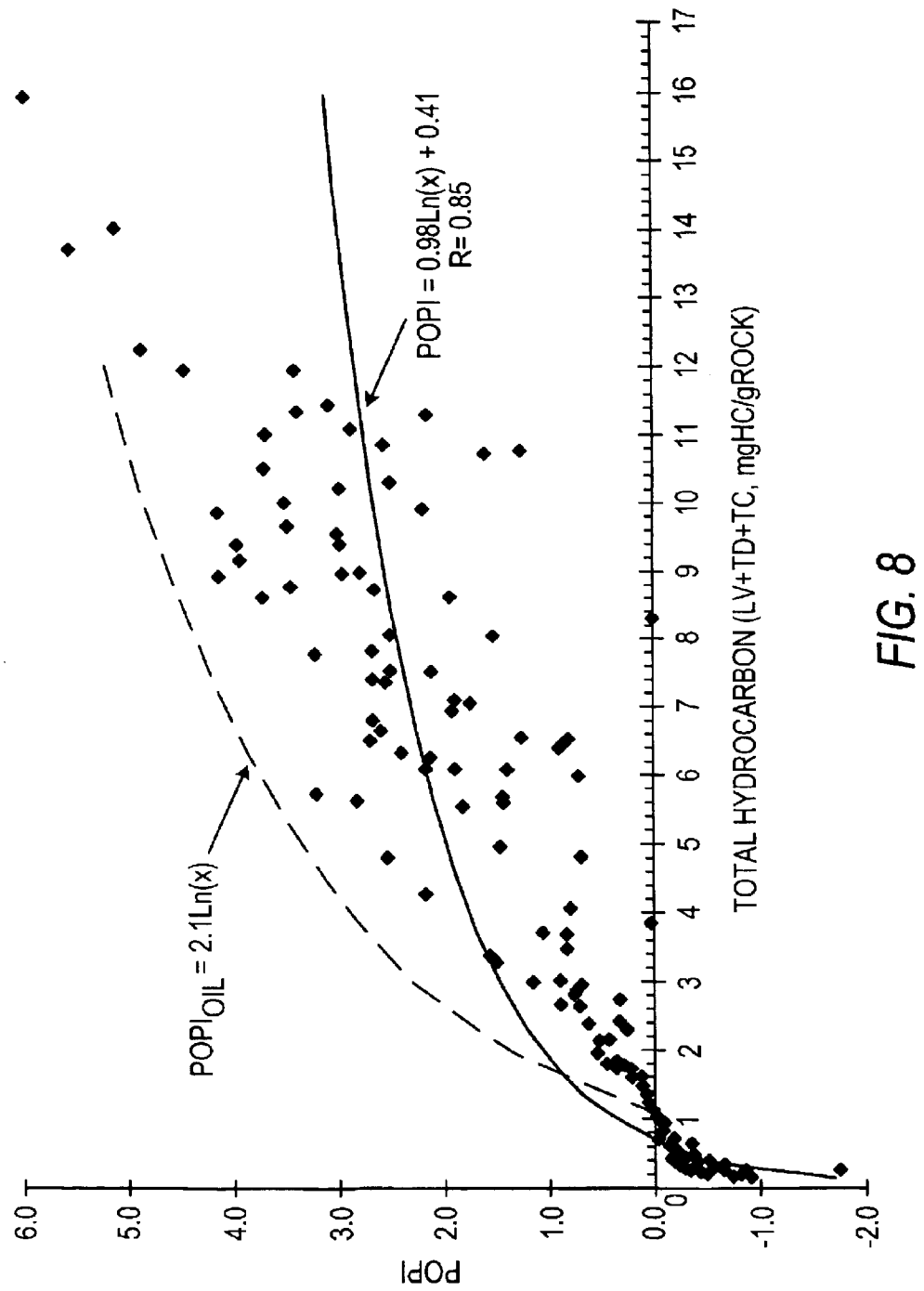
FIG. 8 is an example of curve-fitting POPI versus Total Hydrocarbons to assess PPLC and API gravity.

For reasons that will be described later, POPI data for reservoir rock samples often do not produce a clear trend with most data points falling along a trend line in accordance with equation (5), as, for example, FIG. 8. In such cases, an iterative approach can be employed in accordance with the method of the invention and a hypothetical line for $POPI_{oil}$ can be constructed utilizing various values for the PPLC factor until a satisfactory curve fit is obtained, with the highest POPI values recorded for given total hydrocarbon quantities. The POPI data in this case can be viewed as fitting in the envelope formed by the X-axis and the line described by the equation:

$$POPI_{oil} = PPLC \times \ln(LV+TD+TC).$$

Figure 9:
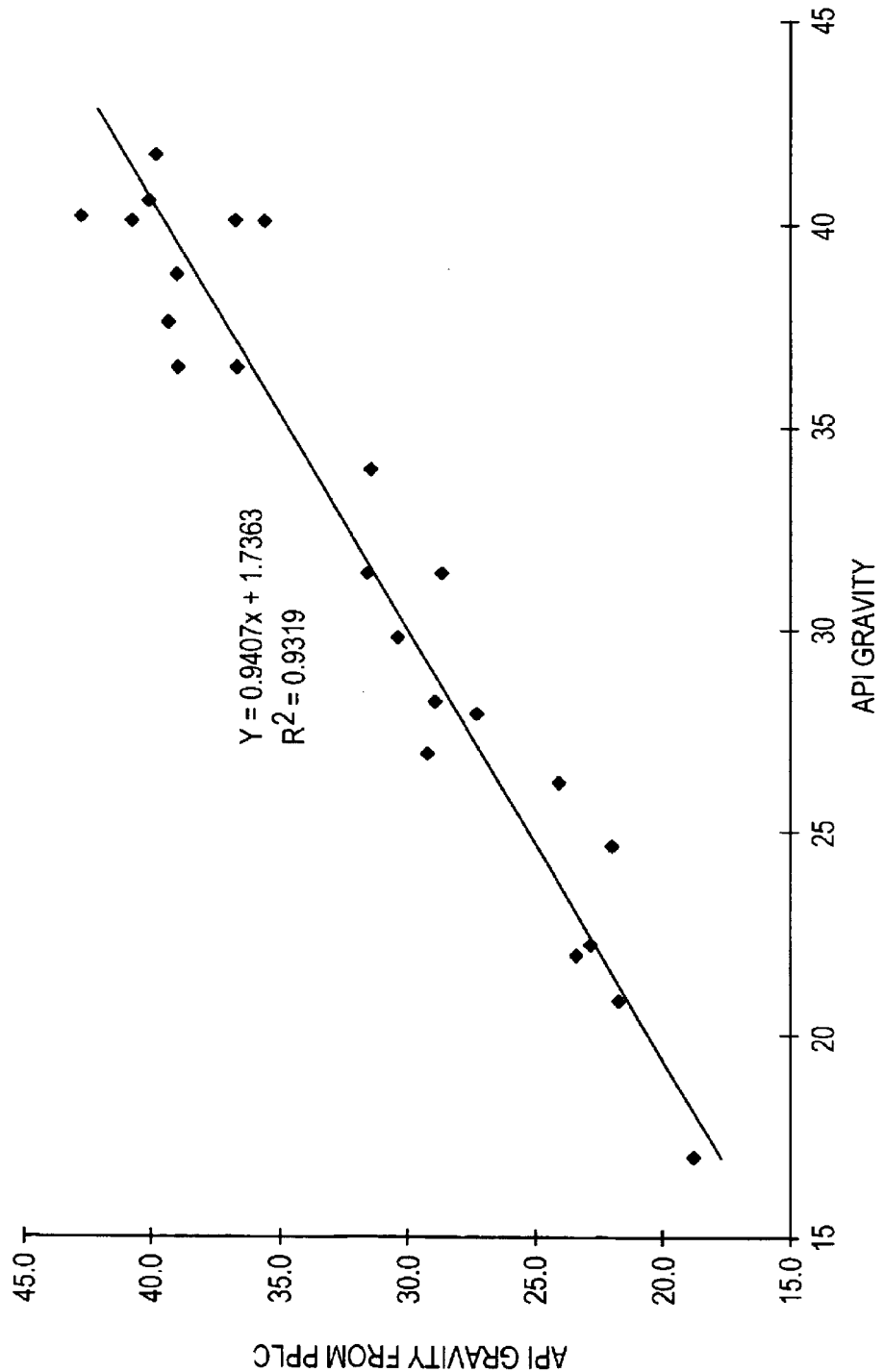
FIG. 9 is a plot of API Gravity computed from PPLC of oils and reservoir rock samples versus the actual API Gravity values determined from the oil samples or from the produced oils from the respective wells with reservoir rock samples.
Figure 10:
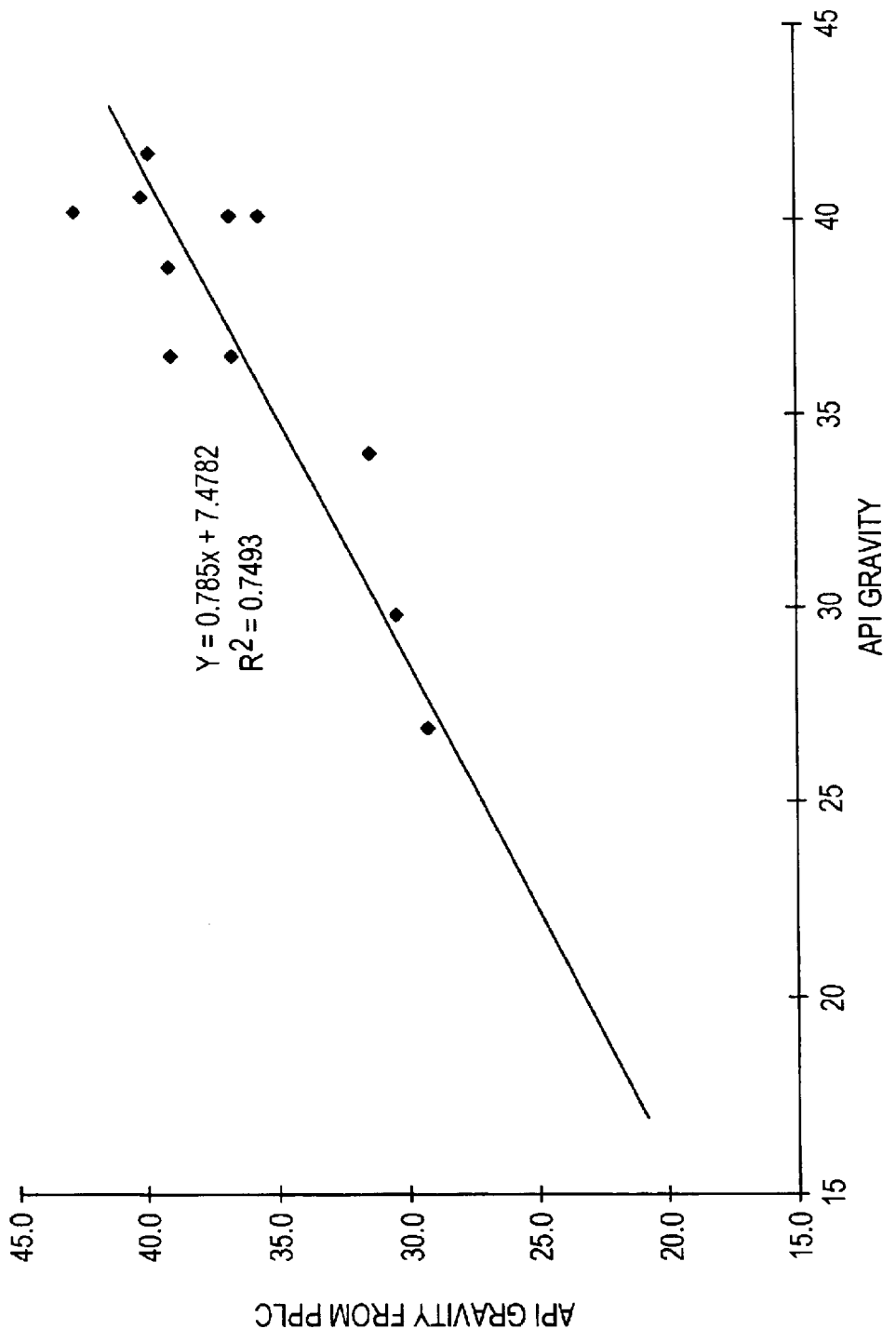
FIG. 10 is a plot of API Gravity from PPLC on reservoir rock samples versus API Gravity measurements of the corresponding oils.

FIG. 9 is a cross plot of API gravity as determined from the PPLC versus measured API gravity for oils and the produced oils from wells corresponding to the reservoir rock samples analyzed. Of particular significance in the method of the invention is the fact that the slope is very close to 1 (0.94), the intercept is small (1.7), and the correlation coefficient is very high (r=0.97). This plot demonstrates that the method of the invention can be employed over a wide range of API gravities and that the difference between the API gravity predicted from PPLC is generally within 2–3 API gravity units, or less. FIG. 10 is the same plot as FIG. 9, but employs only the rock data. For this set of data, the correlation is somewhat lower (correlation coefficient r=0.87) due to the fact that the sample set ranges only from 27–42° API gravity. However, the fit is still good, and the difference between the API gravity and that predicted from the PPLC is generally within 2–3° API, or less.

Determination of Apparent Water Saturation from POPI Data

Figure 11:
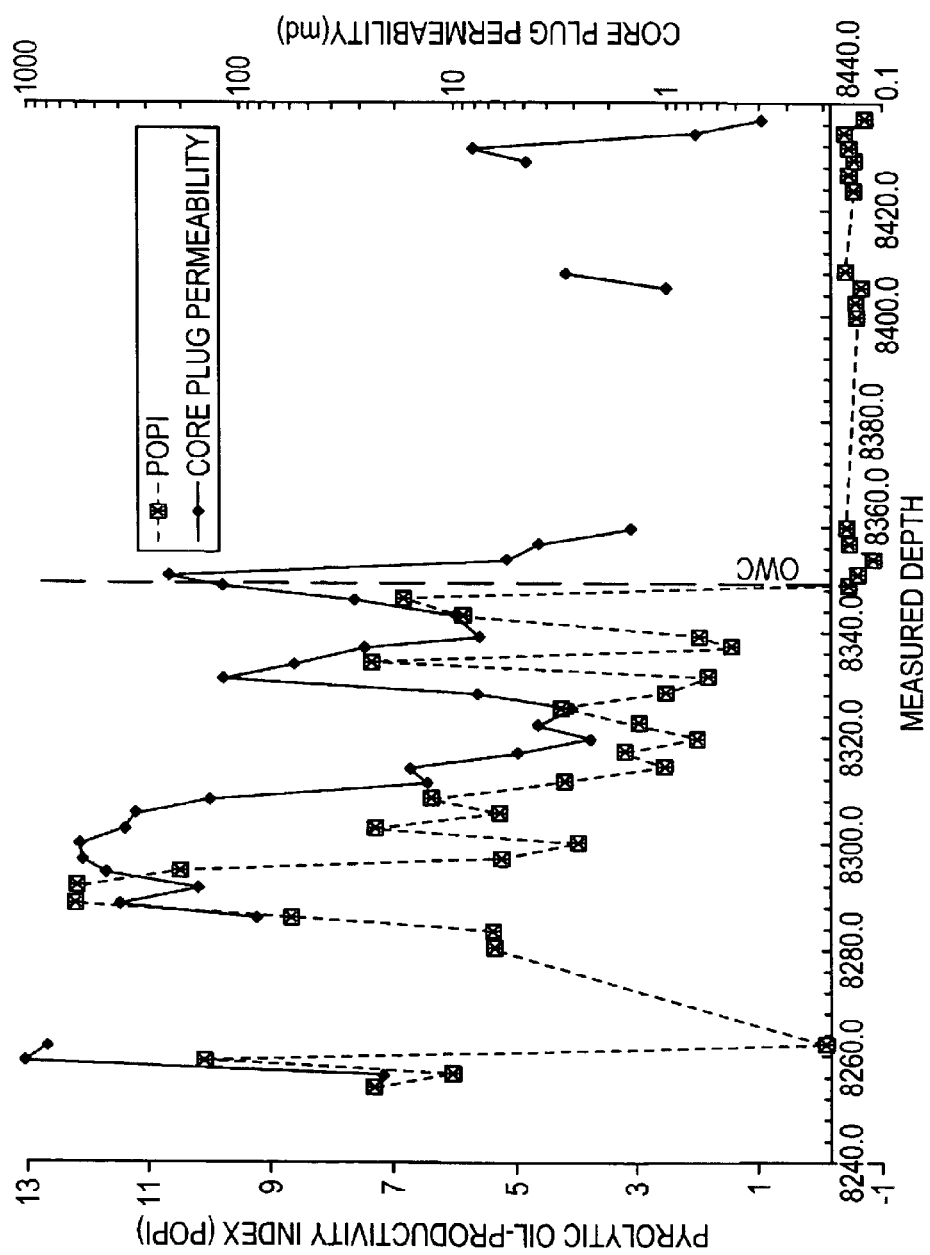
FIG. 11 is a comparative graphic plot of POPI and Core Plug Permeability versus Depth for a well exhibiting a well-lefined oil-water contact.

From an analysis of POPI field data, it was observed that POPI values decrease markedly in oil-water transition zones and that POPI values generally become negative at the base of the transition zone. See, for example, FIG. 11. This is due to two factors: 1) total hydrocarbon saturation decreases with increasing water saturation resulting in decreasing pyrolytic yield; and 2) with increasing water saturation there is a decrease in the proportion of the lighter components (LV and TD) as compared to the asphaltene (thermally crackable, TC) components that comprise the oil.

The increase in heavier (TC) components relative to the lighter components (LV+TD) associated with increasing water saturation is believed to be the result of differential absorption effects. In an oil reservoir, the system begins as rock matrix with water-filled pores. As the reservoir fills with oil, a given portion of the reservoir will experience either sufficient capillary pressure to replace the water with hydrocarbons to a point where the water saturation is at an irreducible level ($S_{wirr}$), or the capillary pressure will be sufficient to displace only a portion of the water in the pores ($S_w > S_{wirr}$). It has been found that the residual staining on the rock matrix resembles the original oil (POPI=$POPI_{oil}$) only when the reservoir has attained (or nearly attained) a condition of irreducible water saturation and that the irreducible water saturation is generally low (e.g., <20%). In this case, the relative absorption A of the components representative of the LV, TD and TC pyrolytic products is similar enough so that the staining matches the oil characteristics very closely, that is $A_{LV} \approx A_{TD} \approx A_{TC}$. However, as the final hydrocarbon saturation for a particular portion of the reservoir results in progressively greater water saturation ($S_w$), the relative absorption of the heavy components (TC) is favored over the lighter components (LV+TD) such that the absorption of LV is less than or approximately equal to the absorption of TD, which is much less than the absorption of TC. This can be expressed mathematically as: $A_{LV} <$, or $\approx A_{TD} << A_{TC}$.

The method of the invention for determining the Apparent Water Saturation ($AS_w$) from pyrolytic data is based upon the recognition of: (1) the above understanding of differential absorption effects, and (2) the generally decreasing hydrocarbon yield associated with increasing water saturation. Two endpoints can be defined that correspond to these conditions: (1) water saturation is at an irreducible level (e.g., $S_w$ is between 0.05 to 0.1 on a pore volume-to-pore volume basis), and the corresponding residual hydrocarbon staining closely resembles the reservoir oil, resulting in a condition where, for a series of reservoir rock samples analyzed, POPI=$POPI_{oil}$; or (2) water saturation is very high ($S_w$=1.00), residual staining does not resemble the reservoir oil ($A_{TC} >> A_{TD} >$, or $\approx A_{LV}$), and total hydrocarbon yield is very low ((LV+TD+TC)$\approx$ or <1.0 mgHC/gRock), resulting in a POPI value that is near or below zero.

Thus, on a plot of POPI versus total hydrocarbons (LV+TD+TC), these two endpoints can be clearly identified. FIG. 7 is an example of a POPI versus total hydrocarbon plot for a well-behaved data set (i.e., the logarithmic fit of the data set for the rock samples results in a high correlation coefficient, r=0.94). In this example, the solid line is the logarithmic fit of the data and the dashed line is the hypothetical line assumed to match the oil characteristics, and as such, is defined as POPI=$POPI_{oil}$. Along the dashed line corresponding to POPI=$POPI_{oil}$, it is assumed that the rock is completely saturated with oil ($S_o$=1.0, $S_w$=0.0) and that any data points falling on this line, or above it, represent rock samples whose pore spaces are fully saturated by oil. Since irreducible water saturations cannot be less than about 0.05 in practice, the line POPI=$POPI_{oil}$ is set to (1−$S_{wirr}$) and any calculated Apparent Oil Saturation ($AS_o$) that exceeds 0.95 is set equal to 0.95. The other line on the plot represents the condition where POPI=0 (the x-axis) and this corresponds to full water saturations ($S_o$=0, $S_w$=1.0). With these two endpoints, the calculation of $AS_o$ and $AS_w$ for any given data point is a simple linear interpolation between the $POPI_{oil}$ value corresponding to the particular total hydrocarbon yield of the sample and the x-axis. Thus, for a given sample "a" with pyrolytic data corresponding to $LV_a$, $TD_a$, and $TC_a$:

$$POPI_a = TD_a + TC_a \times \ln(LV_a + TD_a + TC_a), \quad (1a)$$

$$POPI_{oil,a} = PPLC_{API} \times \ln(LV_a + TD_a + TC_a)$$

$$AS_o = (1 - S_{wirr}) \times POPI_a \div POPI_{oil,a}, \quad (10)$$

and $$AS_{w,a} = 1 - AS_{o,a}. \quad (11)$$

Figure 12:
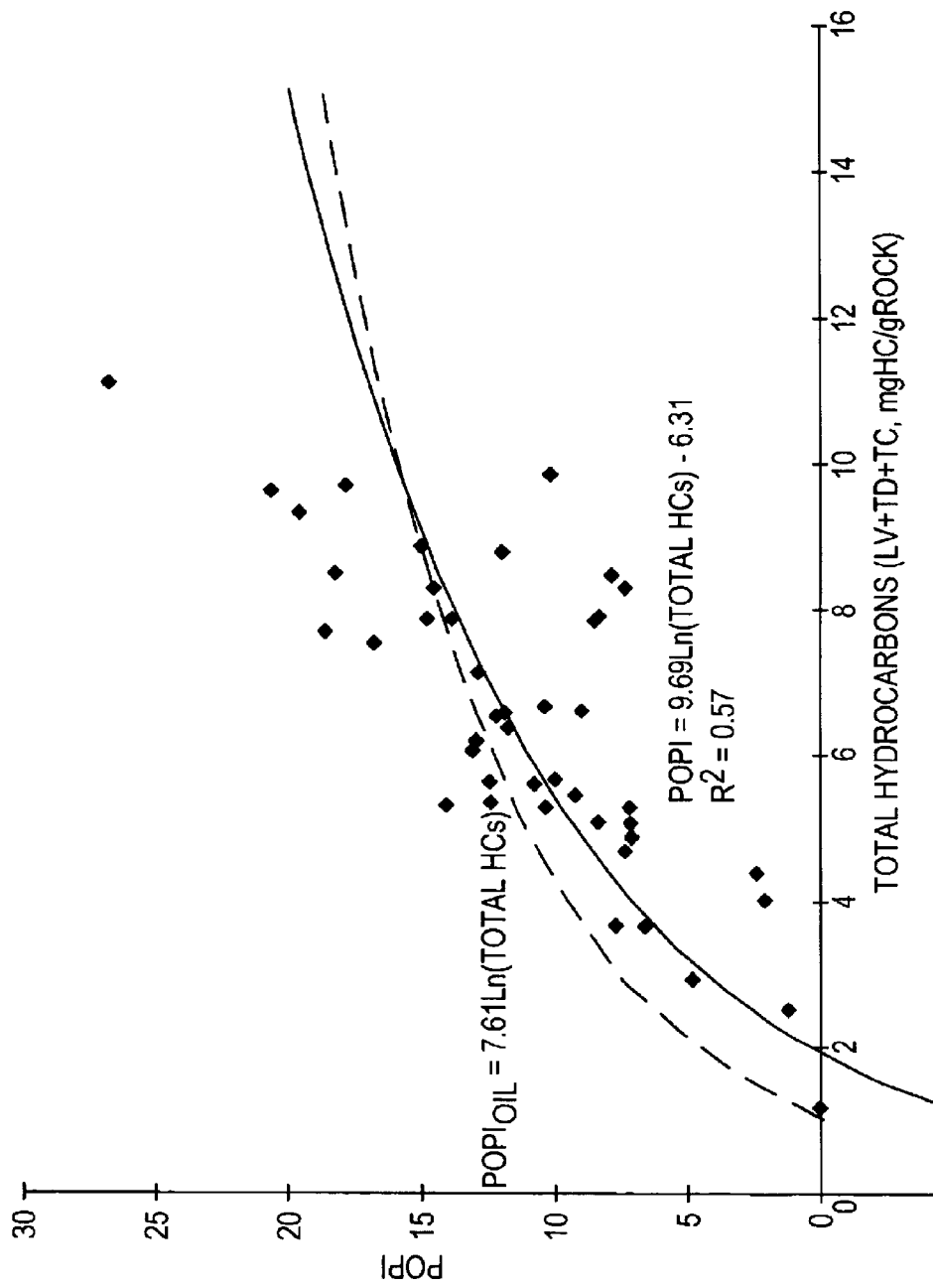
FIG. 12 is a graphic plot of POPI versus Total Hydrocarbons (LV+TD+TC) for a well with a relatively low correlation of the PPLC.

FIG. 12 is an example employing the method to a data set of samples that is not very well-behaved in that the logarithmic fit (solid line) of data results in a low correlation coefficient (r=0.75) and the PPLC is high (9.69) as compared to that predicted from API gravity (7.6), resulting in an API gravity prediction of 42.7° as compared to the actual value of 40.2° for the oil that was produced from the well during testing. For the purpose of calculating the $AS_w$ for this well, use of the PPLC value representative of the actual produced oil (dashed line, FIG. 12) is preferred.

Figure 13:
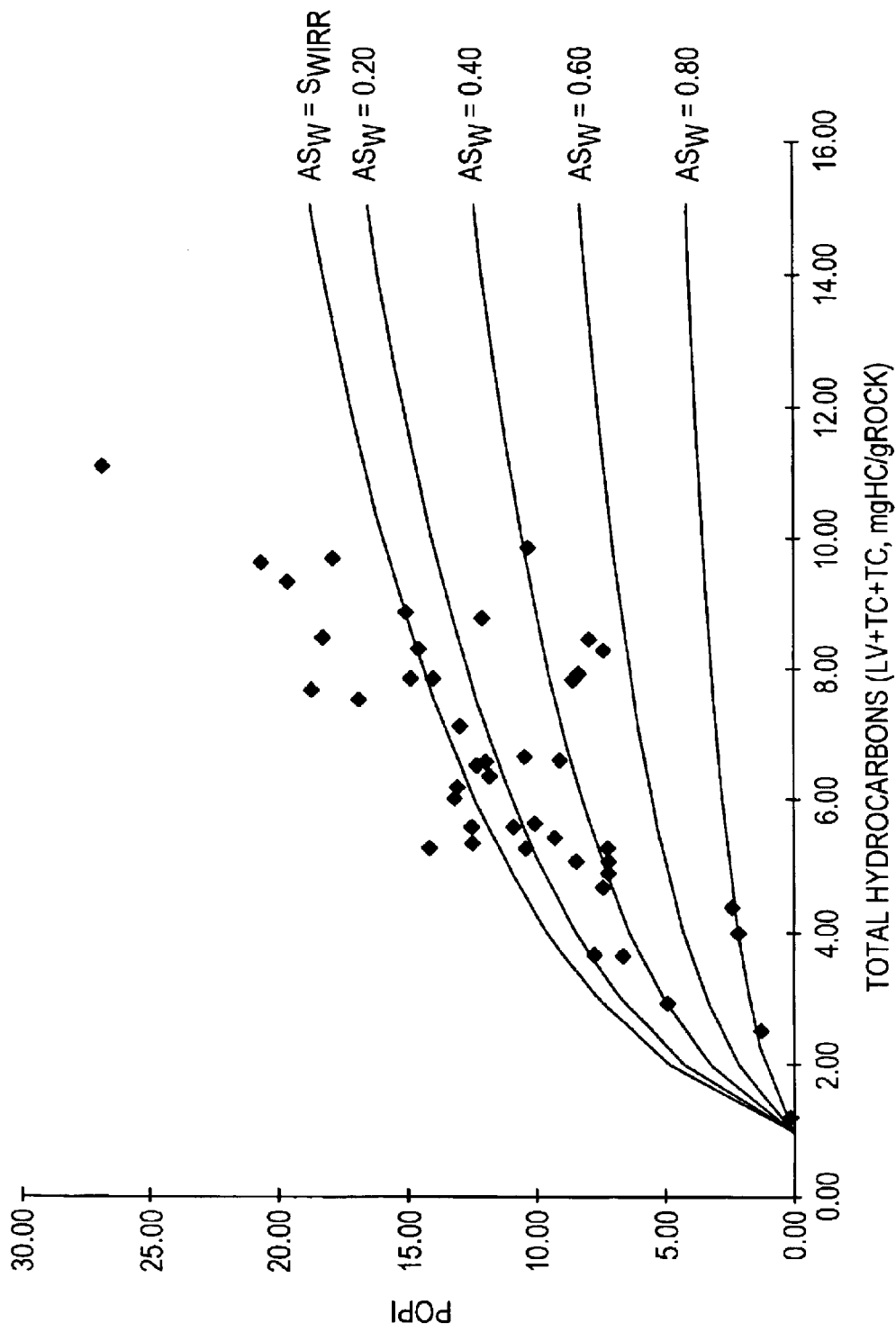
FIG. 13 is a graphic plot of POPI versus Total Hydrocarbons (LV+TD+TC) with iso-$AS_w$ lines separating fields of similar $AS_w$ values.
Figure 14:
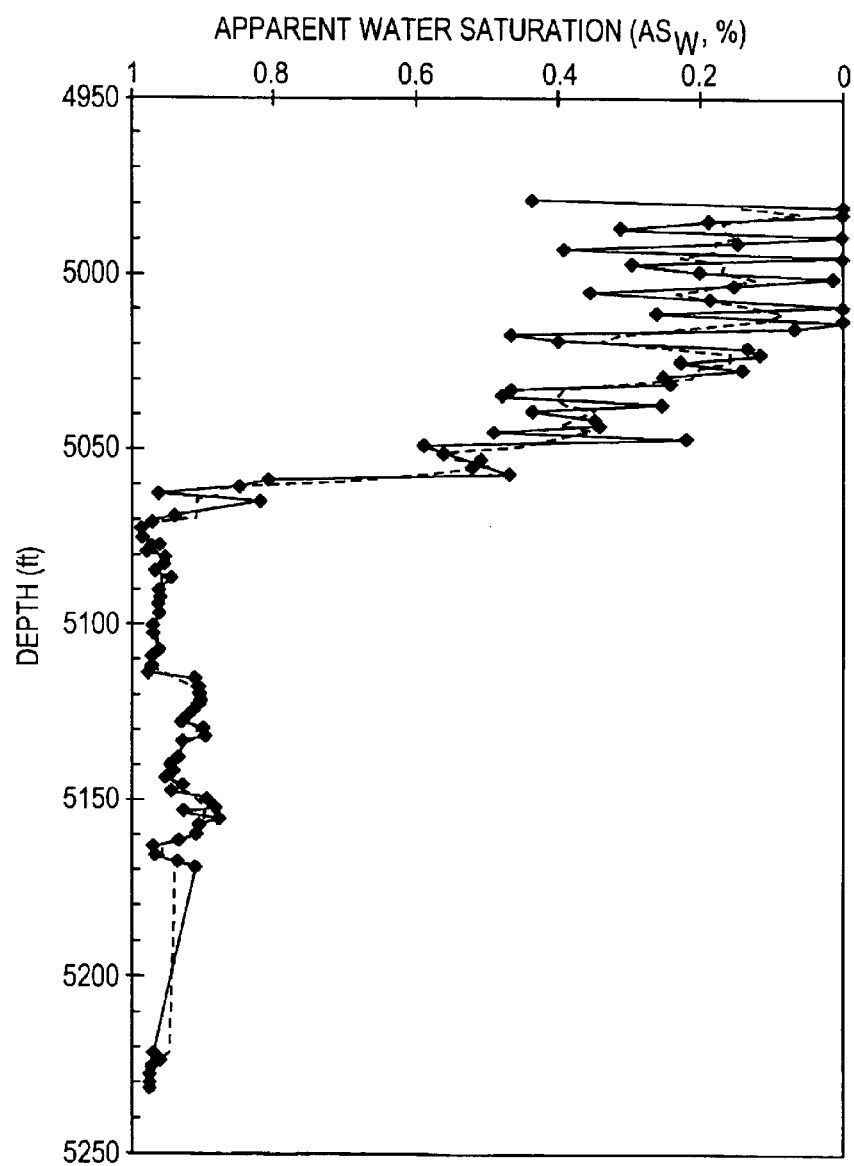
FIG. 14 is a graphic plot of Depth versus Apparent Water Saturation ($AS_w$)

The interpretation of the data can be portrayed graphically, see FIG. 13, by constructing a series of iso-$AS_w$ lines that divide the plot into fields of similar $AS_w$. The interpretation of $AS_w$ for a well is most often portrayed in a Depth versus $AS_w$ plot, as illustrated by FIG. 14. As will be understood from the Depth versus $AS_w$ plots, the $AS_w$ can vary greatly over short depth intervals. $AS_w$ data are most often compared to $S_w$ as determined by the Archie equation. Because of this fact, smoothing the data by using an arithmetic mean applied over a 3–5 ft. interval is a preferred method of simulating the resolution of electric logs with $AS_w$ data, thereby simplifying data comparisons as, for example, the dashed line in FIG. 14.

Another laboratory method to determine water saturation is the "Dean-Stark Method for Oil and Water Saturation Measurement." The application of $AS_w$ has several benefits over the Dean-Stark method, including: (1) the turn-around time is much more rapid than the Dean-Stark method; (2) organic solvents are not used during the pyrolytic technique, resulting in reduced costs and environmental and health benefits; (3) the $AS_w$ method does not require preserved cores, which are much more costly to acquire and later handle to obtain quantitative results; (4) the $AS_w$ method can utilize drill cutting samples; and (5) the $AS_w$ method is accurate over a wider range of oil types, i.e., from API 17° to API 42°.

Figure 15:
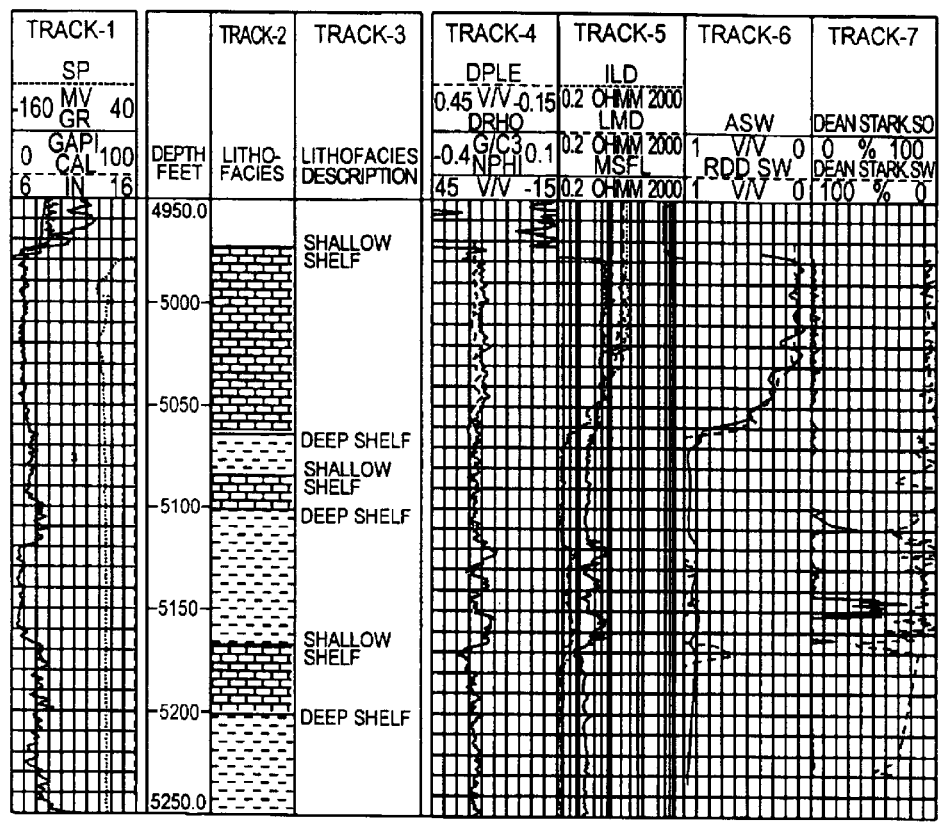
FIG. 15 is a comparative graphic plot of depth profiles on a composite log for Apparent Water Saturations ($AS_w$) from pyrolytic data, and for petrophysical log and derived data obtained by prior art methods.

FIG. 15 is a composite well log that allows the comparison of saturation data from the Dean-Stark method, the $AS_w$ method and $S_w$ from the Archie Equation, to other electric log data. The composite log in FIG. 15 consists of seven log "tracks" with the following information: Track 1 contains the spontaneous potential (SP), gamma ray (GR) and caliper (CAL); Track 2 contains a graphical representation of lithofacies; Track 3 contains lithofacies description in text form; Track 4 contains density porosity (DPLE) and neutron porosity (NPHI); Track 5 contains the deep investigation (ILD), medium investigation (ILM), and shallow investigation (MSFL) restivity logs; Track 6 contains apparent water saturation ($AS_w$), and water saturation ($S_w$) calculated by the Archie Equation (RDD.$S_w$); and Track 7 contains the saturation of oil and water from Dean-Stark analyses that are identified as DEAN-STARK.SO and DEAN-STARK.SW, respectively. In FIG. 15, the apparent water saturation ($AS_w$) and the Archie Equation water saturation ($S_w$, RDD.$S_w$) match very closely. Here, the $AS_w$ data presented are the same as in FIG. 14 and have been smoothed by applying an arithmetic mean over a 3 ft. sample rate. This demonstrates that the $AS_w$ data obtained by the method of the invention are quantitative and comparable to other industry standards for determining water saturation. The Dean-Stark data in comparison, are difficult to interpret. The oil saturation (DEANSTARK.SO) reaches the highest levels well below the actual hydrocarbon column. Also, the water saturation (DEAN-STARK.$S_w$) exhibits only a slight increase, corresponding to the very pronounced oil-water transition zone from 5050 to 5070 ft. The unreliability of the Dean-Stark data in this case is due to not having preserved core samples and the high proportion of light oil in the reservoir (API gravity ~40°). Thus, the method of the invention for estimating the $AS_w$ for the data set is more reliable than the Dean-Stark method.

Calibration of Cementation (m) and Saturation (n) Exponents for Archie Calculations from Electric Logs The most common method utilized in the petroleum industry to determine the saturation of the reservoir rock by water (and hence, by difference, the saturation of hydrocarbons) is the application of the Archie Equation (Archie, 1942; Chen and Fang, 1986) to restivity and porosity electric log data.

The basic Archie Equation, as it is applied in the method of invention, can be expressed as (12):

$$S_w = (1/\phi^m \times R_w/R_t))^{1/n} \qquad (12)$$

where $S_w$ is the water saturation, $\phi$ is the porosity from electric logs, m is the cementation exponent as determined from lab tests, $R_w$ is the formation water restivity as determined from electric logs or as determined by laboratory measurements of formation water samples, $R_t$ is the true resistivity of the formation as measured by deep investigation restivity tools, and n is the saturation exponent as determined by lab tests.

There are a variety of well-known laboratory techniques for the determination of the value of the exponents m and n. However, these techniques are time-consuming and require extensive man-power. Therefore, it has been a common practice in the prior art to determine these parameters empirically by performing iterative applications of the Archie Equation while varying the values of m and n such that reservoirs that are oil-filled ($S_w = S_{wirr}$) and water-filled ($S_w = 1.0$) yield acceptable water saturation values. Having determined acceptable values for m and n, these values are then applied over the entire reservoir interval, making the assumption that the parameters are uniform within the reservoir. This assumption can be reasonable in relatively consistent lithofacies. However, if substantial variations exist in reservoir properties, then significant errors can occur in estimating water saturation, and, therefore, hydrocarbon reserves attributable to a particular well. These errors can have a substantial impact on reservoir management issues and overall project economics.

Figure 16:
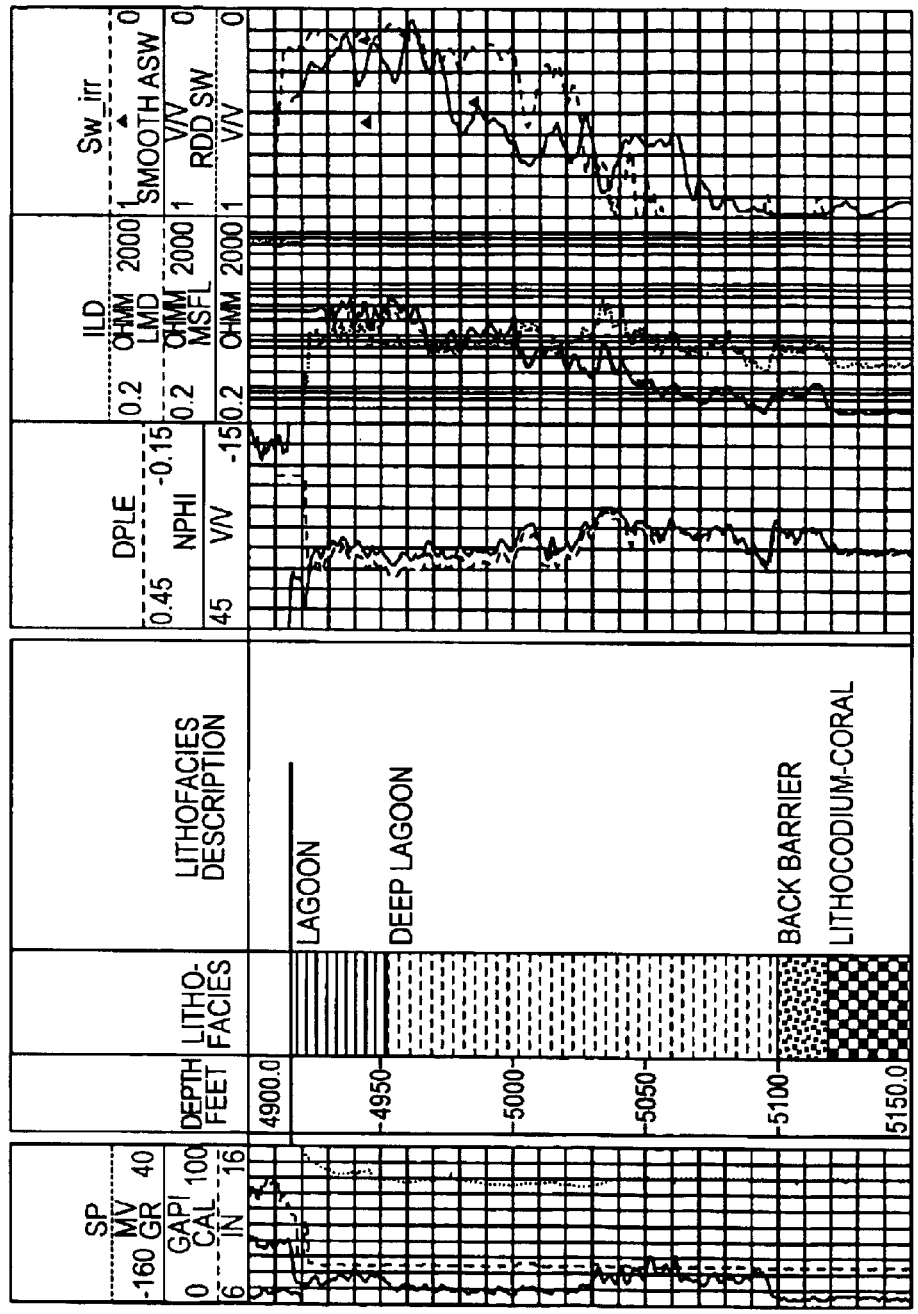
FIG. 16 is a comparative graphic plot of depth profiles presented on a composite well log for Apparent Water Saturation ($AS_w$) as calculated from pyrolytic data, and for petrophysical log and derived data obtained by prior art methods.

The method of the invention for estimating the $AS_w$ also yields another method for calibrating the values of m and n for the purpose of improving the accuracy of the Archie Equation calculations. In one embodiment, the method of the invention comprehends performing iterative applications of the Archie Equation while varying the value of m and n such that the calculated $S_w$ as determined by the Archie Equation closely matches that determined by the $AS_w$ method. An example of employing this technique is illustrated by the following:

Two-hundred-thirty-five core samples taken from a single well were analyzed by pyrolysis using the methods described in U.S. Pat. No. 5,866,814 and summarized above. The sampling interval was from 4918.8 ft. to 5306.7 ft., i.e., about 388 ft. FIG. 16 is a composite well log consisting of basic electric log data, lithofacies descriptions, and in Track-6, apparent water saturation ($AS_w$, SMOOTH.$AS_w$) as calculated from pyrolytic data, water saturation ($S_w$) as calculated by the Archie Equation, (RDD.$S_w$) from electric log data, and individual values for irreducible water saturation ($S_{wirr}$) as determined by laboratory analyses. In general, the Archie calculated and pyrolytic $S_w$ values closely agree between 4920 ft. and 4973 ft. Below 4973 ft., however, the $AS_w$ data have a consistently higher Apparent Water Saturation ($AS_w$) than that calculated by the Archie Equation from electric log data (RDD.$S_w$). The cause for the inconsistency is apparently due to a lessening of reservoir quality, which would produce either a higher irreducible water saturation ($S_{wirr}$), or a considerably different capillary pressure curve with a correspondingly longer transition zone. The determination of irreducible water saturation on core plug samples by the laboratory analyses, in this case, assists in identifying the cause of these differences. Below is a table of the values for $S_{wirr}$, cementation exponent (m), and saturation exponent (n) values for four (4) core samples as determined in the lab.

| Core Depth | $S_{wirr}$ | m | n |
|---|---|---|---|
| 4945.6 | 0.15 | 2.20 | 1.89 |
| 4946.1 | 0.54 | 2.18 | 2.99 |
| 4961.5 | 0.12 | 2.10 | 1.92 |
| 4986.6 | 0.45 | 1.94 | 1.8 |

As shown by the above data and the plot in FIG. 16, the $S_{wirr}$ can vary widely over a very short interval. Moreover, the range of variation is equivalent to the magnitude of the variation of the $AS_w$ values where the samples are located sufficiently above the oil-water transition zone such that $S_w = S_{wirr}$. In FIG. 16, the samples down to 4986.6 ft. correspond to the $AS_w$ data, indicating that the relative increases of $AS_w$ over Archie $S_w$ are the result of increasing irreducible water saturation values. Below 4986 ft., the fact that the $AS_w$ values are generally above the $S_w$ values indicates that either these samples are from an oil-water transition zone, or there is an increase in the $S_{wirr}$ value. Another significant observation regarding the differences in the $AS_w$ and Archie $S_w$ data is the approximately 25 ft. of significant hydrocarbon saturation below the base of the hydrocarbon column for the Archie $S_w$ curve (RDD.$S_w$, 5040 to 5065 ft.). This indicates the presence of better than average reservoir properties in this zone than would be inferred from the application of uniform m and n values.

Figure 17:
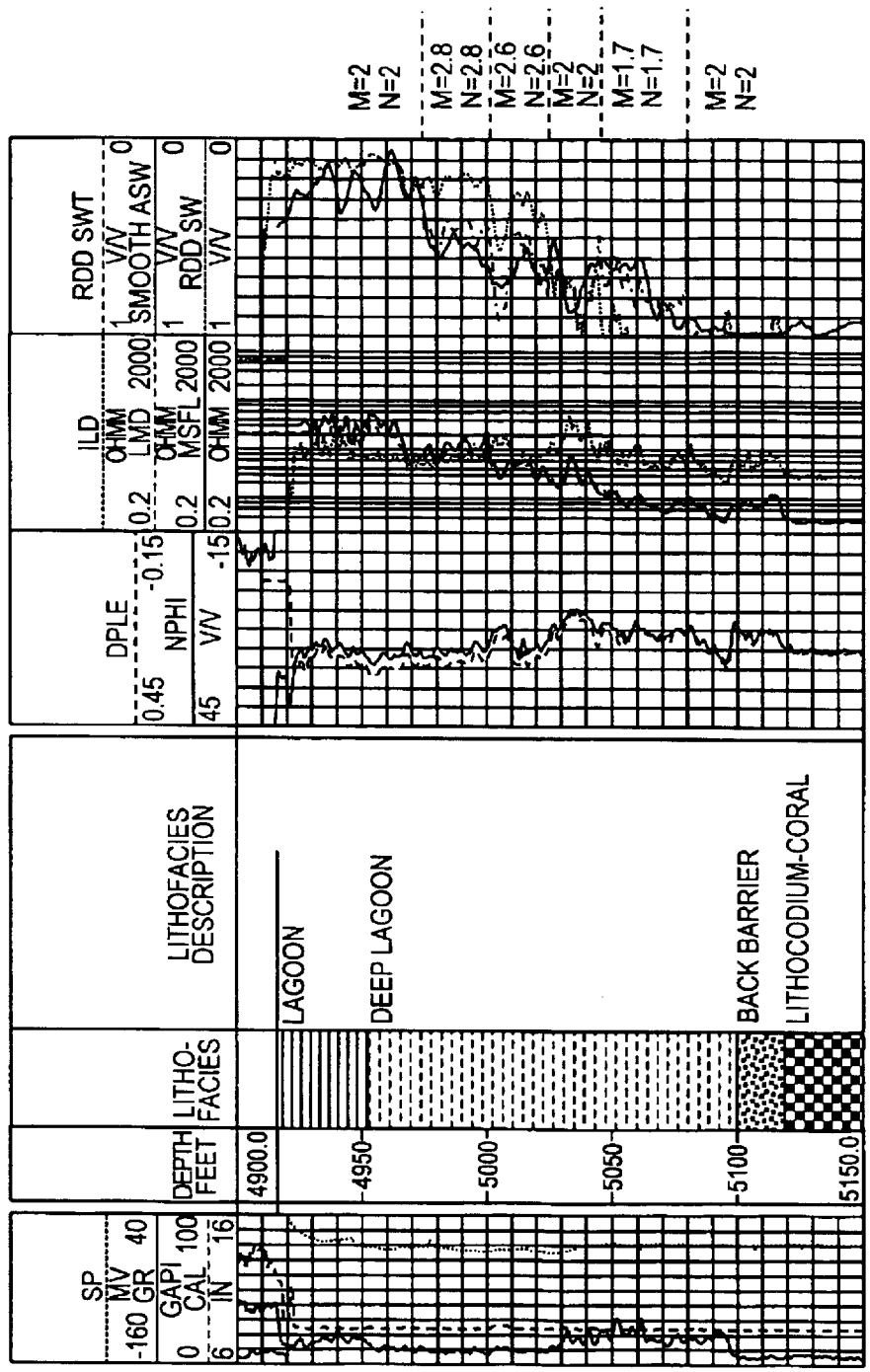
FIG. 17 is a comparative graphic plot of depth profiles on a composite well log that includes Apparent Water Saturation ($AS_w$) as calculated from pyrolytic data, recalculated water saturation using variable cementation (m) and saturation (n) exponent values as annotated, and petrophysical log and derived data obtained by prior art methods.

As a means of assessing the variation in reservoir quality and its effect on the cementation and saturation exponents, the $S_w$ determined from electric logs was recalculated using variable cementation and saturation exponent values to solve the Archie Equation to produce results or values that closely match the $AS_w$ data. The recalculated $S_w$ values are shown in FIG. 17 (Track-6, RDD.$S_w$T). The values for the cementation exponent (m) and the saturation exponent (n) that were used for the various portions of the curve are annotated at the right hand side of the figure.

As can be seen from FIG. 17, reservoir sections between 4920 ft. and 4975 ft., between 5025 and 5045 ft., and below 5080 ft. have $S_w$ and $AS_w$ values that are fairly close. Therefore, m and n have been left at the uniform value of 2.0 that has been applied in this reservoir. Over the rest of the reservoir, several intervals of differing m and n values ranging from 1.7 to 2.8 are employed to shift the recalculated Archie curve (RDD.$S_w$T) to provide a more consistent match with the $AS_w$ values. Adjustments required in order to match $S_w$ as calculated from data obtained by electric logs with the $AS_w$ values (m and n>2) suggest that poorer reservoir quality is present in zones with $AS_w$ values substantially higher than the corresponding $S_w$ values. Likewise, where $AS_w$ is less than $S_w$, then the reservoir quality is predicted to be somewhat better than the average.

Importantly, the range of variation in the values of the m and n exponent values required to match $AS_w$ data to $RDD.S_w$ data is comparable to the values determined from direct petrophysical analysis of core samples. This fact demonstrates that the inferred m and n values obtained by matching $AS_w$ and $S_w$ curves are meaningful, and that the method of the invention provides an accurate and effective improvement for calibrating these important input parameters for reservoir characterization and modeling.

We claim:

1. An improved method for presenting pyrolytic oil-productivity index (POPI) data for characterizing reservoir rock from different geological regions A and B, the method comprising:

a) providing a $POPI_{o(A)}$ value for the region A;

b) calculating the value for a normalizing factor $F_{NORM(A)}$ for the region A in accordance with equation (2A):

$$F_{NORM(A)} = \frac{100}{POPI_{o(A)}}; \tag{2A}$$

c) applying the normalizing factor for a given reservoir rock sample "a" from the region A in accordance with the following equation (3A):

$$F_{NORM(A)} \times POPI_{(a)} = POPI_{NORM(A)(a)}; \tag{3A}$$

d) recording the value of $POPI_{NORM(A)(a)}$;

e) providing a $POPI_{o(B)}$ value for the region B;

f) calculating the value for a normalizing factor $F_{NORM(B)}$ for region B in accordance with equation (2B):

$$F_{NORM(B)} = \frac{100}{POPI_{o(B)}}; \tag{2B}$$

g) applying the normalizing factor for a given reservoir rock sample "a" from the region B in accordance with the following equation (3A¹):

$$F_{NORM(B)} \times POPI_{(a)} = POPI_{NORM(B)(a)}; \tag{3A¹}$$

and h) recording the value of $POPI_{NORM(B)(a)}$, whereby the values of $POPI_{NORM(A)(a)}$ and $POPI_{NORM(B)(a)}$ are directly comparable to determine the relative quality of the reservoir rock in the regions A and B.

2. The method of claim 1 where the normalization factors $F_{NORM(A)}$ and $F_{NORM(B)}$ are applied to a plurality of values $POPI_{(A)(X)}$ and $POPI_{(B)(X)}$ associated with a corresponding plurality of reservoir rock samples "x" obtained from regions A and B, whereby the POPI data so normalized is directly comparable to determine the relative quality of the corresponding reservoir rock samples from regions A and B.

3. The method of claim 1 where the POPI data are recorded in an electronic data storage device associated with a general purpose computer.

4. The method of claim 3 where the values of $POPI_{o(A)}$ and $POPI_{o(B)}$ are provided by accessing the data storage device.

5. The method of claim 4 where the general purpose computer is programmed to calculate the normalizing factors for each of the plurality of datum from the regions A and B, to apply the normalizing factors for each of the plurality of POPI datum selected for each of the regions A and B and to transfer normalized data to the data storage device.

6. The method of claim 1 where the value of $POPI_{o(A)}$ or $POPI_{o(B)}$, or both, is calculated in accordance with equation (7):

$$POPI_o = PPLC \times \ln(HC_{min}), \tag{7}$$

where

PPLC is the POPI Pre-Logaritunic Coefficient and is a constant for a given type of oil;

ln is the natural logarithm; and $HC_{min}$ is assigned a value in the range of 4 to 6 mg HC/gram of rock; and the value of PPLC is determined by utilizing a logarithmic fit of POPI and (LV+TD+TC) data points for a plurality of rock samples in accordance with equation (5):

$$POPI = PPLC \times \ln(LV+TD+TC) \tag{5}$$

where (LV+TD+TC) is the total quantity of hydrocarbons in a sample.

7. The method of claim 1 where the value of $POPI_{o(A)}$ or $POPI_{o(B)}$, or both, is calculated in accordance with equation (7):

$$POPI_o = PPLC \times \ln(HC_{min}), \tag{7}$$

where the terms are as defined above, and the value of PPLC is calculated in accordance with equation (6A):

$$PPLC = 0.151 \times e^{(0.0976 API)} \tag{6A}$$

where API is the numerical value of the API gravity.

8. The method of claim 1 where the value of $POPI_{o(A)}$ or $POPI_{o(B)}$, or both, is calculated in accordance with equation (6C):

$$API = \frac{\ln(PPLC/0.151)}{0.0970} \tag{6C}$$

9. A method of normalizing data derived by application of the POPI method to a plurality of sets of reservoir rock samples $X_n$ obtained from a plurality of geophysical regions $A_n$, the data comprising a single value of $POPI_o$ derived for each of the plurality of regions $A_n$ and a set of values of $POPI_X$ for the rock samples $X_n$ obtained from each region, the method comprising the steps of:

a) calculating the value for a normalizing factor $F_{NORM(A)}$ for each of the regions $A_n$ in accordance with $$F_{NORM(A)} = \frac{100}{POPI_{o(A)}};$$

b) applying the normalizing factor in accordance with the following $$F_{NORM(A)} \times POPI_{o(A)} = POPI_{NORM(A)};$$

c) applying the normalizing factor to each value in the data set comprising the set for the corresponding region in accordance with:

$$F_{NORM(A)} \times POPI_{X(A)} = POPI_{NORM(XA)};$$

and d) recording the data resulting from steps (b) and (c) above.

10. A method for estimating the API gravity value of oil contained in reservoir rock proximate a well bore hole $X_n$ located in region A, where the region A has produced oil at a plurality of different locations exhibiting different known API gravity values, the method comprising the steps of:

a) recording data sets corresponding to the POPI values and the Total Hydrocarbons (LV+TD+TC) for each of the oils having a different known API gravity and for the well $X_n$;

b) fitting a separate logarithmic curve to each of the separate data sets recorded in step (a) in accordance with formula (4):

$$POPI = PPLC \times \ln(LV+TD+TC) + b \qquad (4)$$

c) preparing a graphic plot of the PPLC value versus the API gravity for each of the oils having a different known API gravity;

d) locating the position on the graphic plot for the PPLC value associated with the data set of well $X_n$;

e) identifying the API gravity value for well $X_n$ corresponding to the PPLC from the graphic plot; and f) recording the estimated API gravity as identified in step (e) for the oil in the reservoir rock proximate well $X_n$.

11. The method of claim 10 where the data are recorded in an electronic memory device associated with a programmable computer, said computer being provided with a program adapted to perform steps (b) through (f); the method further comprising operating said programmed computer to perform steps (b) through (f) and displaying the API gravity value as recorded in step (f) on display means.

12. The method of claim 11 where the display means are selected from the group consisting of a monitor associated with the computer and printed paper record.

13. A method of estimating the API gravity value of oil contained in reservoir rock from an oil field region A based on the pyrolytic oil-producing index, POPI, of good quality reservoir rock in the region A, the method comprising the steps a) providing a set of POPI data;

b) preparing a plot of the POPI values versus total hydrocarbons (LV+TD+TC);

c) fitting a logarithmic curve to the plot of step (b) by application of a POPI Pre-logarithmic Coefficient, PPLC, having an empirically-determined numerical value;

d) solving the following equation (9) for API gravity:

$$POPI_o = PPLC \times \ln(577 \times API^{-1.38}),$$

where $POPI_o$ is the value for good quality reservoir rock and PPLC is determined in accordance with step (c), above, and e) recording the value of API gravity.

14. A method of estimating the API gravity value for oil contained in reservoir rock proximate a well bore hole $X_n$ located in a region A, where the region A has produced oil exhibiting a plurality of different known API gravity values, the method comprising the steps of:

a) providing a separate graphical plot of POPI values versus Total Hydrocarbons (LV+TD+TC) for each of the plurality of oils having a different known API gravity, all of said plots being to the same scale;

b) fitting a logarithmic curve to each of the separate graphic plots provided in step (a) in accordance with the equation (5):

$$POPI_{oil} = PPLC \times \ln(LV+TD+TC); \qquad (5)$$

c) preparing a plot of PPLC versus API gravity for the set of oils fitting an exponential curve to the data in accordance with equation (6):

$$PPLC = PEC \times e^{(c \times API)} \qquad (6)$$

d) preparing a plot of POPI versus Total Hydrocarbons (LV+TD+TC) from rock samples obtained from well bore hole $X_n$, said plot being to the same scale as the plurality of plots prepared in step (b);

e) fitting a logarithmic curve to the graphic plot prepared in step (d) in accordance with equation (5);

$$POPI_{oil} = PPLC \times \ln(LV+TD+TC) \qquad (5)$$

f) comparing the PPLC determined from rock samples with the plot of PPLC versus API gravity of oil samples to determine the approximate of API gravity of oil in the reservoir rock; and g) recording the estimated value of the API gravity of oil proximate well bore hole $X_n$.

15. The method of claim 14 where the POPI values for the plurality of oils of known API gravity are derived from core samples.

16. The method of claim 15 where the core samples are not specially preserved.

17. The method of claim 14 which comprises the further steps of entering the POPI values and Total Hydrocarbon values in the memory of a programmable computer that has been programmed to calculate the value of PPLC for each of the plurality of oils having a known API gravity and for the samples from well $X_n$.

18. The method claim 17 which further comprises directing the computer to compare the data and display the API gravity value or values that correspond to the PPLC for well $X_n$.

19. The method of claim 18 where the data displayed comprises a graphic plot of POPI values versus Total Hydrocarbons for the well $X_n$ and for at least the one closest oil of known API gravity.

20. An improved method for characterizing reservoir rock from an oil well bore hole based on a set of conventional water saturation values for a given length of the bore hole over an interval L as calculated from the Archie Equation, the improvement characterized by:

a) providing a plurality of reservoir rock samples "a" taken from known positions along the interval L;

b) calculating the value of the pyrolytic oil productivity index ($POPI_a$) for each of the rock samples "a" in accordance with equation (1a):

$$POPI_a = \ln(LV_a + TDa + TC_a) \times (TDa \div TC_a) \qquad (1a)$$

c) recording the calculated $POPI_a$ values in a data set in conjunction with the position of the sample along the interval L;

d) providing the value of PPLC by:

(i) plotting POPI versus (LV+TD+TC) and obtaining a logarithmic fit of the data, or (ii) plotting POPI versus (LV+TD+TC) and iteratively fitting a logarithmic line of the equation $POPI_{oil}=$ PPLC×ln(LV+TD+TC) by varying the value of PPLC until most of the data fit within the region between the line describing POPI=POPI$_{oil}$ and the X-axis (POPI=0);

(iii) utilizing the known relationship between API gravity in a region and the PPLC to solve for the PPLC using a value selected from the expected or actual API gravity for oil produced from a well;

(e) calculating and recording POPL$_{oil}$ values for each reservoir rock sample "a" in accordance with equation (5);

$$POPI_{oil,a}=PPLC \times \ln(LV_a+TD_a+TC_a) \quad (5)$$

(f) recording the calculated POPI$_{oil,a}$ values in a data set in conjunction with the position of the sample along interval L;

g) calculating the Apparent Water Saturation value, AS$_w$, from the POPI values in accordance with the following equations (10) and (11):

$$AS_o=(1-S_{wirr}) \times POPI_a \div POPI_{oil,a} \quad (10)$$

and $$AS_{W,a}=1-AS_{o,a} \quad (11)$$

h) recording the calculated AS$_w$ values in a data set in conjunction with the position of the corresponding sample along the interval L; and i) comparing the data set of conventional S$_w$ values derived from the Archie Equation with the data set of AS$_w$ values derived from the POPI values for a particular length along the interval L, whereby variations between the two data sets indicate changes in the character of the reservoir rock.

21. The method of claim 20, where the rock samples are rock cuttings.

22. The method of claim 20 where the values of the data sets are recorded in an electronic data storage device associated with a computer.

23. The method of claim 20 where the values of the data sets for S$_w$ and AS$_w$ are plotted graphically.

24. The method of claim 23 where the graphic plots are to the same linear scale along the interval L.

25. The method of claim 24 where the graphic plots are positioned proximate each other to facilitate the comparison.

26. The method of claim 25 which includes the further step of providing with the graphic plots of AS$_w$ and S$_w$ at least one other corresponding graphic plot of a data set from along the interval L selected from the group consisting of electric log data, lithofacies and Dean-Stark data.

27. The method of claim 20 where the known positions along the interval L are the depth below the earth's surface.

28. The method of claim 20 which includes recalibrating the exponential cementation values m and n for the Archie Equation (12):

$$S_w=(1/\phi^m \times R_w/R_t)^{1/n} \quad (12)$$

where

S$_w$ is the water saturation,

φ is the porosity from electric logs, m is the cementation exponent as determined from lab tests, R$_w$ is the formation water restivity as determined from electric logs or as determined by laboratory measurements of formation water samples, R$_t$ is the true resistivity of the formation as measured by deep investigation restivity tools, and n is the saturation exponent as determined by lab tests, the method comprising the steps of:

a) applying at least one iterative change to the value of at least one of the exponents m and n;

b) recalculating the value of S$_w$ from the Archie Equation;

c) recording the value of S$_w$ obtained from step (b);

d) comparing the value of S$_w$ recorded in step (c) to the value of AS$_w$;

e) repeating steps (a) through (d) above until the values of S$_w$ closely match the values of AS$_w$.

29. The method of claim 28, where the value of both m and n are varied for at least one of the iterations.

30. The method of claim 28 where the value of S$_w$ is recalculated at a plurality of locations along the interval L.

31. The method of claim 28 which comprises the further step of graphically plotting the values of AS$_w$ and the recalculated S$_w$ values to the same linear scale, whereby the relative matching of the values of AS$_w$ and S$_w$ is accomplished visually.

32. The method of claim 31 which comprises the step of providing with the graphic plots of AS$_w$ and recalculated S$_w$ at least one other corresponding graphic plot of a data set from along the interval L selected from the group consisting of electric log data, lithofacies and Dean-Stark data.

* * * * *